United States Patent
Kay et al.

(10) Patent No.: US 9,150,882 B2
(45) Date of Patent: Oct. 6, 2015

(54) SELF-COMPLEMENTARY PARVOVIRAL VECTORS, AND METHODS FOR MAKING AND USING THE SAME

(75) Inventors: Mark A. Kay, Los Altos, CA (US); Dirk Grimm, Palo Alto, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 928 days.

(21) Appl. No.: 11/701,279

(22) Filed: Jan. 31, 2007

(65) Prior Publication Data

US 2007/0253936 A1    Nov. 1, 2007

Related U.S. Application Data

(60) Provisional application No. 60/764,179, filed on Jan. 31, 2006.

(51) Int. Cl.
*C12N 15/86* (2006.01)
*A61K 48/00* (2006.01)

(52) U.S. Cl.
CPC .............. *C12N 15/86* (2013.01); *A61K 48/005* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 4,766,072 | A | 8/1988 | Jendrisak et al. |
| 6,294,379 | B1 * | 9/2001 | Dong et al. ................ 435/320.1 |
| 6,547,099 | B1 | 4/2003 | Farris |
| 2002/0006664 | A1 | 1/2002 | Sabatini |
| 2002/0045264 | A1 * | 4/2002 | During et al. ................ 435/456 |
| 2003/0139363 | A1 | 7/2003 | Kay et al. |
| 2003/0153519 | A1 | 8/2003 | Kay et al. |
| 2004/0029106 | A1 | 2/2004 | Samulski et al. |

FOREIGN PATENT DOCUMENTS

| | | |
|---|---|---|
| WO | WO 00/28061 A2 | 5/2000 |
| WO | WO 01/68836 A2 | 9/2001 |
| WO | WO 01/92551 A2 | 12/2001 |
| WO | WO 02/063025 A2 | 8/2002 |
| WO | WO 03/010180 A1 | 2/2003 |

OTHER PUBLICATIONS

Yan et al. Inverted terminal repeat sequences are important for intermolecular recombination and circularization of adeno-associated virus genomes. Journal of Virology, vol. 79, No. 1, pp. 364-379, Jan. 2005.*
Duan et al. Circular intermediates of recombinant adeno-associated virus have defined structural characteristics responsible for long-term episomal persistence in muscle tissue. Journal of Virology, vol. 72, No. 11, pp. 8568-8577, Nov. 1998.*
GenBank Accession No. AF043303, GI: 2906016, publicly available Feb. 1998.*
GenBank Accession No. U48704, GI: 1408467, publicly available Jul. 1996.*
GenBank Accession No. U89790, GI: 2337938, publicly available Aug. 1997.*
Xia et al. RNAi suppresses polyglutamine-induced neurodegeneration in a model of spinocerebellar ataxia. Nature Medicine, vol. 10, No. 8, pp. 816-820, 2004.*
Ahern, H. Biochemical, Reagents Kits Offer Scientists Good Return on Investment. The Scientist, vol. 9, No. 15, p. 20, Jul. 1995, printed as pp. 1/7 to 7/7.*
Ahern, Biochemical, reagents kits offer scientists good return on investment. The Scientist, vol. 9, No. 15, p. 20, 1995, printed as pp. 1/7-7/7.*
Chiorini et al., "Cloning of Adeno-Associated Virus Type 4 (AAV4) and Generation of Recombinant AAV4 Particles", *Journal of Virology*, 71(9):6823-6833 (1997).
Samulski et al., "Rescue of Adeno-Associated Virus From Recombinant Plasmids: Gene Correction within the Terminal Repeats of AAV", *Cell*, 33(1):135-143 (1983).
International Search Report and Written Opinion for PCT application PCT/US2007/002712, search report dated Feb. 26, 2008, 11 pages (2008).
Hirata et al., *J. Virology*, 74:4612-4620 (2000).
McCarty et al., *Gene Therapy*, 8:1248-1254 (2001).
Grimm et al., *Nature*, 441:537-541 (2006).

* cited by examiner

*Primary Examiner* — Jennifer Dunston
(74) *Attorney, Agent, or Firm* — Bozicevic, Field & Francis LLP; Kyle A. Gurley

(57) ABSTRACT

The teachings herein are generally directed to a method of enhancing the genetic stability of parvovirus vectors. The stability of conventional ss or dsAAV vector constructs can be enhanced, for example, to obtain a concurrent increase in vector titer and purity, as well as an improvement in vector safety, due at least in part to the elimination of stuffer DNA from the AAV vector. The method is broadly applicable to all gene transfer/therapy applications, such as those requiring delivery of foreign DNA containing recombinant gene expression cassettes. Such foreign DNA can range, for example, from about 0.2 up to about 5.2 kb in length. The enhanced vector constructs are highly flexible, user-friendly, and can be easily modified (via routine DNA cloning) and utilized (via standard AAV vector technology) by anyone skilled in the art.

28 Claims, 8 Drawing Sheets

```
        T
      T T
      C G
      C G
      A T
      G C
      A T
      G C
      G C
      T A
      C G  GGCCGAGTGAGTGAGCGAG-3'
      T     CCGGCTCACTCACTCGCTCGCGC-5'
      G C
      A T
      C G              BssHII
      G C
      G C
      C G
      C G
      G C
      G C
      A A
      G
```

AAV-4 ITR
(SEQ ID NO:1)

FIG. 1C gagttaataattaccagcgcgggccaaataaataatcgcgaggggcaggtgacgtttgcccagcgcgcgctggtaattattaacctcgcgaat
attgattcgaggccgcgattgccgcaatcgcgaggggcaggtgacctttgcccagcgcgcgttcgccccgccccggacggtatcgatgtcga
gggggatcccactgggaggatgttgagtaagatggaaaactactgatgacccttgcagagacagagtattaggacatgtttgaacaggggcc
gggcgatcagcaggtagctctagaggtaccccagatctagtgtctgtctgcacatttcgtagagcgagtgttccgatactctaatctccctaggca
aggttcatatttgtgtaggttacttattctccttttgttgactaagtcaataatcagaatcagcaggtttggagtcagcttggcagggatcagcagcct
gggttggaaggaggggggtataaaagccccttcaccaggagaagcccagctgggcgcgccggatccttaattaaATGCAGCGCGTG
AACATGATCATGGCAGAATCACCAGGCCTCATCACCATCTGCCTTTTAGGATATCTACTCAGTGC
TGAATGTACAggtttgtttcattaaaaacaaagactttcttaagagatgtaaaattttcatgatgttttcttttttgctaaaactaaagaattattctt
ttacatttcaGTTTTTCTTGATCATGAAAACGCCAACAAAATTCTGAATCGGCCAAAGAGGTATAATTCA
GGTAAATTGGAAGAGTTTGTTCAAGGGAACCTTGAGAGAGAATGTATGGAAGAAAAGTGTAGTTT
TGAAGAAGCACGAGAAGTTTTTGAAAACACTGAAAGAACAACTGAATTTTGGAAGCAGTATGTTG
ATGGAGATCAGTGTGAGTCCAATCCATGTTTAAATGGCGGCAGTTGCAAGGATGACATTAATTCC
TATGAATGTTGGTGTCCCTTTGGATTTGAAGGAAAGAACTGTGAATTAGATGTAACATGTAACATT
AAGAATGGCAGATGCGAGCAGTTTTGTAAAAATAGTGCTGATAACAAGGTGGTTTGCTCCTGTAC
TGAGGGATATCGACTTGCAGAAAACCAGAAGTCCTGTGAACCAGCAGTGCCATTTCCATGTGGA
AGAGTTTCTGTTTCACAAACTTCTAAGCTCACCCGTGCTGAGGCTGTTTTTCCTGATGTGGACTAT
GTAAATTCTACTGAAGCTGAAACCATTTTGGATAACATCACTCAAAGCACCCAATCATTTAATGAC
TTCACGCGTGTTGTTGGTGGAGAAGATGCCAAACCAGGTCAATTCCCTTGGCAGGTTGTTTTGAA
TGGTAAAGTTGATGCATTCTGTGGAGGCTCTATCGTTAATGAAAAATGGATTGTAACTGCTGCCC
ACTGTGTTGAAACTGGTGTTAAAATTACAGTTGTCGCCGGCGAACATAATATTGAGGAGACAGAA
CATACAGAGCAAAAGCGAAATGTGATTCGAATTATTCCTCACCACAACTACAATGCAGCTATTAAT
AAGTACAACCATGACATTGCCCTTCTGGAACTGGACGAACCCTTAGTGCTAAACAGCTACGTTAC
ACCTATTTGCATTGCTGACAAGGAATACACGAACATCTTCCTCAAATTTGGATCTGGCTATGTAAG
TGGCTGGGGAAGAGTCTTCCACAAAGGGAGATCAGCTTTAGTTCTTCAGTACCTTAGAGTTCCAC
TTGTTGACCGAGCCACATGTCTTCGATCTACAAAGTTCACCATCTATAACAACATGTTCTGTGCTG
GCTTCCATGAAGGAGGTAGAGATTCATGTCAAGGAGATAGTGGGGGACCCCATGTTACTGAAGT
GGAAGGGACCAGTTTCTTAACTGGAATTATTAGCTGGGGTGAAGAGTGTGCAATGAAAGGCAAA
TATGGAATATATACCAAGGTATCCCGGTATGTCAACTGGATTAAGGAAAAAACAAAGCTCACTTAA
ttaagtctagagtcgacctagaactagtaataaaggatcctttattttcattggatccgtgtgttggttttttgtgtgcggccgcgtcga (SEQ ID NO:2)

FIG. 5

SELF-COMPLEMENTARY PARVOVIRAL VECTORS, AND METHODS FOR MAKING AND USING THE SAME

CROSS-REFERENCE

This application claims the benefit of U.S. Provisional Application No. 60/764,179, filed Jan. 31, 2006.

STATEMENT REGARDING FEDERALLY SPONSORED RESEARCH OR DEVELOPMENT

This invention was made, in part, with government support under grant number NIH/NHLBI RO1 HL64274 from the National Institute of Health. The United States government has certain rights to this invention.

SEQUENCE LISTING

The instant application contains a sequence listing which has been submitted as a paper copy and a computer readable format that is hereby incorporated herein by reference in its entirety.

BACKGROUND

1. Field of the Invention

The teachings herein are generally directed to a method of enhancing the genetic stability of parvovirus vectors.

2. Description of Related Art

Parvoviruses are among the smallest, simplest eukaryotic viruses and fall into two groups: defective viruses that are dependent on a helper virus for replication; and autonomous, replication-competent viruses. Adeno-associated viruses are non-pathogenic, helper-dependent members of the parvovirus family. One of the identifying characteristics of this group of viruses is the encapsidation of a single-stranded DNA (ssDNA) genome. In the case of AAV, the separate plus or minus polarity strands are packaged with equal frequency, and either is infectious. At each end of the ssDNA genome, a palindromic terminal repeat (ITR) structure base-pairs upon itself into a hairpin configuration. This serves as a primer for cellular DNA polymerase to synthesize the complementary strand after uncoating in the host cell. Being helper dependent, the adeno-associated viruses generally require a helper virus for a productive infection.

Recombinant adeno-associated virus (rAAV) vectors have great potential for use in nucleic acid delivery applications, since rAAV vectors provide a number of advantages over other viral vectors. For example, rAAV vectors are capable of transducing nondividing cells and do not induce an immune response that eliminates the host cells. Like the wild type virus, nucleic acid delivery vectors derived from adeno-associated virus (AAV) can package and deliver single-stranded DNA genomes. Unfortunately, although otherwise very promising, the conventional AAV vectors have major limiting factors.

The main problem with the current generation of AAV gene transfer/therapy vectors is their genetic instability. Conventional AAV vectors typically consist of a recombinant gene expression cassette (promoter—gene—termination signal), flanked by the inverted terminal repeats (ITRs) of AAV. The ITRs are typically 145 bp long sequences derived from the very ends of the AAV genome and serve as DNA replication as well as packaging (or encapsidation) signals. In the current generation of AAV vectors, these ITRs are usually derived from a particular AAV sero/genotype, AAV-2 (the prototype of the AAV family) and are identical to each other. Such vectors can accommodate up to ~5.2 kb of foreign DNA and are usually referred to as single-stranded AAV (ssAAV, wild-type AAV is also a single-stranded virus).

Recent reports show that this inherent limitation of AAV vectors can be overcome by the use of genomes that are half the length of the virus wild-type, and these genomes can be packaged as dimeric DNA molecules in an inverted repeat configuration (See Hirata and Russell and Russell, J. Virol. (2000) 74:4612-4620; McCarty et al., Gene Ther. (2001) 8:1248-1254; each of which are hereby incorporated herein by reference in its entirety). Such preparations thus have largely varying efficiencies and require labor-intensive purification and enrichment steps.

Each of the following is hereby incorporated herein in its entirety by reference: U.S. Published Application Nos. 20020006664, 20030153519, and 20030139363; U.S. Pat. Nos. 6,547,099; 6,506,559; and 4,766,072; PCT Application Nos. WO 01/92551, WO 01/68836, and WO 03/010180. Recently, U.S. Published Application No. 20040029106 ("Samulsky") teaches a modification termed double-stranded (ds) or self-complementary (sc) AAV, where one of the two AAV-2. ITRs carries a specific deletion of 6 nt, the so-called terminal resolution site (trs). The purpose of this deletion is as follows: during replication of a conventional ssAAV vector genome, a ds intermediate is formed and then subsequently resolved via nicking at the trs site. In the trs-deleted dsAAV version, this nicking reaction is ablated. As a result, the replication of these vectors becomes arrested at the ds intermediate step. This intermediate, containing two inverted copies of the recombinant gene expression cassette separated by the mutated ITR, then becomes encapsidated. In transduced cells, the two inverted copies of an expression cassette (each copy up to 2.2 kb in size) rapidly re-fold and anneal with each other, resulting in an immediate and strong onset of gene expression from dsAAV vectors. In contrast, standard ssAAV transduce substantially more slowly and less efficiently, because two individual complementary DNA strands have to "find" each other in the cell, which is a rate-limiting step.

Despite the increase in transduction efficacy, these dsAAV vectors share a substantial problem with ssAAV vectors—genetic instability during propagation, as observed in E. coli, as well as during in vitro manipulation of the vector plasmids. This is because both ss and dsAAV vectors carry identical (or nearly identical, when considering the 6 bp deletion in one ITR in dsAAV) ITRs, making them extremely prone to homologous recombination. A frequent result (~50%) is either deletion of large parts (>20 bp) of one ITR, or gene conversion between the two ITRs. The latter is a particular problem with dsAAV, as it results in repair of the 6 bp deletion and consequently loss of the desired ds genotype.

Another related adverse consequence is a drop in vector particle titers. In fact, typical vector particle yields obtained with conventional dsAAV vectors are about 5-10 fold lower than what is possible with ssAAV vectors. Moreover, such standard dsAAV preparations usually contain a mixture of actual dsAAV genomes, together with half-sized monomers which result from ITR repair and subsequent nicking. And, it is very difficult to purify the wanted dsAAV vector particles from the contaminating monomers.

Moreover, the genetic instability of ss or dsAAV vectors with two (nearly) identical ITRs increases inversely with the insert size, making it impossible to clone inserts smaller than ~2.5 kb into a conventional ssAAV vector, or smaller than ~1 kb into dsAAV. Such minimal inserts are highly desirable for certain human gene therapy applications, where the recombinant gene expression cassette is small, such as for an interfering RNA (RNAi; typically <0.6 kb). In these cases, conventional vectors require the addition of stuffer DNA sequences, to increase the insert size to >1 (dsAAV) or 2.5 (ssAAV) kb. The presence of additional stuffer DNA is highly unwanted, as these sequences could cause serious adverse events in the patient, including an immune reaction.

Accordingly, one of skill will appreciate a nucleic acid construct that overcomes at least these limitations of both conventional ss or dsAAV vectors. The constructs taught herein overcome the problems of genetic instability, the resulting low titers, vector impurities and the need for stuffer DNA, thus providing a novel and valuable contribution to the art.

SUMMARY OF THE INVENTION

The teachings herein are generally directed to a method of enhancing the genetic stability of parvovirus vectors. The process for creating a stabilized parvovirus vector begins with creating a parvovirus vector genome template nucleic acid. The template nucleic acid includes a 5' inverted terminal repeat (ITR) and a 3' ITR, each flanking an end of a foreign DNA domain. The nucleotide sequence of either the 5' ITR or 3' ITR is a heterologous ITR having a sequence that is less than 90% complementary to the other ITR sequence to prevent ITR repair or conversion and create the stabilized parvovirus vector. As a result, the stabilized parvovirus vector produced using the template nucleic acid is more stable than it would have been if created without the presence of the heterologous ITR in the template nucleic acid.

In some embodiments, either the 5' or 3' ITR does not contain a functional terminal resolution site, such that the nucleic acid creates a double-stranded vector. The 5' ITR or 3' ITR can be an AAV-4 ITR. In some embodiments, the 5' ITR or 3' ITR can be a synthetic ITR containing a rep protein binding site and having a hairpin secondary structure.

In some embodiments, the foreign DNA domain encodes a protein. In some embodiments the foreign DNA encodes an RNAi product such as, for example, an shRNA or micro-RNA. In some embodiments, the foreign DNA domain comprises one or more expression cassettes, each independently ranging in size from about 0.2 kb to about 2.2 kb, and adding up to a total size of no more than 2.4 kb.

In some embodiments, the vectors are a stabilized, double-stranded parvovirus vector produced by the template nucleic acid. The double-stranded vectors include two inverted copies of a foreign DNA comprising a nucleotide sequence (5'-3') and a complementary (3'-5') nucleotide sequence in a double-stranded configuration; a heterologous inverted terminal repeat (ITR) separating the two inverted copies, wherein the heterologous ITR does not contain a functional terminal resolution site; and, a 5' ITR and a 3' ITR, wherein the 5' ITR and the 3' ITR sequences are substantially complementary to each other to allow for recombination. The stabilized parvovirus vector is more stable than it would have been if created without the presence of the heterologous ITR in the template nucleic acid In some embodiments, the vectors are a stabilized, single-stranded parvovirus vector produced by the template nucleic acid. The single-stranded vector includes a 5' inverted terminal repeat (ITR) and a 3' ITR, each flanking an end of a foreign DNA domain. The nucleotide sequence of either the 5' or 3' ITR is a heterologous ITR having a sequence that is less than 90% complementary to the other ITR sequence to prevent ITR repair or conversion and create a stabilized parvovirus vector. Accordingly, the stabilized parvovirus vector is more stable than it would have been if created without the presence of the heterologous ITR in the template nucleic acid. The stabilized parvovirus vector is more stable than it would have been if created without the presence of the heterologous ITR in the template nucleic acid.

In some embodiments, the parvovirus is an adeno-associated virus such as, for example, AAV-2. In some embodiments, the heterologous ITR is an AAV-4 ITR. In some embodiments, the heterologous ITR is a synthetic ITR containing a rep protein binding site and having a hairpin secondary structure. In some embodiments, the foreign DNA domain comprises one or more expression cassettes, each independently ranging in size from about 0.2 kb to about 5 kb, and adding up to a total size of no more than about 5 kb.

In some embodiments, the invention includes a parvovirus virion comprising a parvovirus capsid and a stabilized, double-stranded parvovirus vector. In some embodiments, the invention includes a parvovirus virion comprising a parvovirus capsid and a stabilized, single-stranded parvovirus vector. In some embodiments, the invention includes a composition comprising a parvoviral virion containing a stabilized, parvoviral vector, wherein the parvoviral virion is in a pharmaceutically acceptable carrier.

In some embodiments, the invention includes cell comprising a stabilized, double-stranded parvovirus vector. In some embodiments, the invention includes a cell comprising a stabilized single-stranded parvovirus vector.

In some embodiments, the invention includes a method of producing a virion, comprising introducing the nucleic acid template into a cell that permits parvovirus replication; introducing an AAV helper plasmid to provide rep and cap genes; introducing an adenoviral helper plasmid to provide helper-virus function; and maintaining the cell under conditions sufficient to produce a stabilized parvoviral vector, package the vector in a parvovirus capsid, and produce the virion.

In some embodiments, the invention includes a method for introducing the nucleic acid template into at least one cell of a multicellular host, the method comprising administering to the multicellular host an effective amount of a virion containing a stabilized, parvoviral vector, so that the nucleic acid is introduced into at least one cell of the multicellular host. In many embodiments, the multicellular host is a mammal. In some embodiments, the nucleic acid contains a cassette for expressing FIX to induce clotting, and in these embodiments, the clotting can be induced to treat hemophilia, such as hemophilia B.

In some embodiments, the invention includes a kit for use in producing the virions taught herein. The kit includes a plasmid comprising the nucleic acid template, or components for producing the same; an AAV helper plasmid to provide rep and cap genes, or components for producing the same; an adenoviral helper plasmid to provide helpervirus function, or components for producing the same; and, instructions for producing the virion.

BRIEF DESCRIPTION OF THE FIGURES

FIGS. 1A-1C illustrate an improved design of double-stranded vector genomes according to some embodiments.

FIG. 5 illustrates the sequence for the FIX expression cassette.

DETAILED DESCRIPTION OF THE INVENTION

Figure 1A:
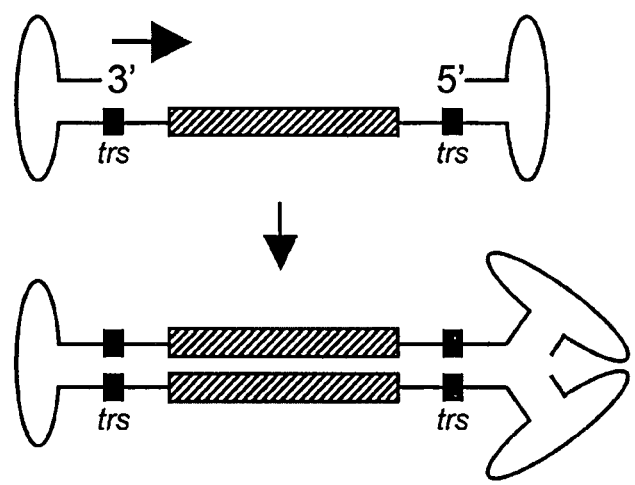

The teachings herein are generally directed to a method of enhancing the genetic stability of parvovirus vectors. The stability of conventional ss or dsAAV vector constructs can be enhanced, for example, to obtain a concurrent increase in vector titer and purity, as well as an improvement in vector safety, due at least in part to the elimination of stuffer DNA from the AAV vector. The method is broadly applicable to all gene transfer/therapy applications, such as those requiring delivery of foreign DNA containing recombinant gene expression cassettes. Such foreign DNA can range, for example, from about 0.2 up to about 5.2 kb in length. The enhanced vector constructs are highly flexible, user-friendly, and can be easily modified (via routine DNA cloning) and utilized (via standard AAV vector technology) by anyone skilled in the art.

DEFINITIONS

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission and in accordance with 37 CFR §1.822 and established usage.

Except as otherwise indicated, standard methods known to those skilled in the art may be used for the construction of recombinant parvovirus and rAAV constructs, packaging vectors expressing the parvovirus rep and/or cap sequences, as well as transiently and stably transfected packaging cells. Such techniques are known to those skilled in the art. See, e.g., Sambrook et al., Molecular Cloning, A Laboratory Manual 2d ed. (Cold Spring Harbor, N.Y., 1989); F. M. Ausubel et al. Current Protocols in Molecular Biology (Green Publishing Associates, Inc. and John Wiley & Sons, Inc. New York).

The term "parvovirus" as used herein refers to DNA animal viruses that contain a linear, single-stranded DNA genome and encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, mouse minute virus, bovine parvovirus, canine parvovirus, chicken parvovirus, feline, panleukopenia virus, feline parvovirus, goose parvovirus, and B19 virus. Other autonomous parvoviruses are known to those skilled in the art.

The genus Dependovirus contains the adeno-associated viruses (AAV), including but not limited to, AAV type 1, AAV type 2, AAV type 3, AAV type 4, AAV type 5, AAV type 6, avian AAV, bovine AAV, canine AAV, equine AAV, and ovine AAV. See, e.g., Bernard N. Fields et al., Virology, vol. 2, ch. 69 (3d ed., Lippincott-Raven Publishers).

As used herein, the term "vector" or "gene delivery vector" may refer to a parvovirus (e.g., AAV) particle that functions as a gene delivery vehicle, and which comprises the vector genome packaged within a parvovirus capsid. Alternatively, in some contexts, the term "vector" may be used to refer to the vector genome DNA.

A "heterologous nucleotide sequence" will typically be a sequence that is not naturally-occurring in the virus. Alternatively, a heterologous nucleotide sequence may refer to a viral sequence that is placed into a non-naturally occurring environment (e.g., by association with a promoter with which it is not naturally associated in the virus).

As used herein, a "recombinant parvovirus vector genome" is a parvovirus genome into which a heterologous (e.g., foreign) nucleotide sequence (e.g., transgene) has been inserted. A "recombinant parvovirus particle" comprises a recombinant parvovirus vector genome packaged within a parvovirus capsid.

Likewise, a "rAAV vector genome" is an AAV genome that comprises a heterologous nucleotide sequence. rAAV vectors require only the 145 base terminal repeats in cis to generate virus. All other viral sequences are dispensable and may be supplied in trans (Muzyczka, (1992) Curr. Topics Microbiol. Immunol. 158: 97). Typically, the rAAV vector genome will only retain the minimal terminal repeat (ITR) sequences so as to maximize the size of the transgene that can be efficiently packaged by the vector. A "rAAV particle" comprises a rAAV vector genome packaged within an AAV capsid.

The inventive parvovirus particles may be a "hybrid" particle in which the viral ITRs and viral capsid are from different parvoviruses. The viral ITRs and capsid may be from different serotypes of AAV, e.g., as described in international patent publication WO 00/28004, U.S. Provisional Application No. 60/248,920; and Chao et al., (2000) Molecular Therapy 2: 619; each of which is hereby incorporated herein in its entirety. Likewise, the parvovirus may have a "chimeric" capsid (e.g., containing sequences from different parvoviruses, preferably different AAV serotypes) or a "targeted" capsid (e.g., a directed tropism) as described in international patent publication WO 00/28004.

In certain embodiments, the vector genomes are "duplexed" parvovirus genomes which may interchangeably be referred to herein as dimeric or self-complementary vector genomes. The parvovirus particles of the invention comprise a parvovirus capsid containing at least one virion DNA genome which is self-complementary so that it may form a hairpin structure upon release from the viral capsid. The duplexed parvovirus vector genomes typically contain sufficient packaging sequences for encapsidation within the selected parvovirus capsid (e.g, AAV capsid). Those skilled in the art will appreciate that the duplexed genome may not exist in a double-stranded form under all conditions, but has the ability to do so under conditions that favor annealing of complementary nucleotide bases. Accordingly, the term "duplexed parvovirus vector genome" does not indicate that the genome is necessarily in duplexed or double-stranded form (e.g., there is base-pairing between the self-complementary strands) within the parvovirus capsid. Indeed, one skilled in the art will understand that the genome DNA is likely not in a double-stranded form while packaged within the parvovirus capsid.

The term "template" is used herein to refer to a polynucleotide sequence that may be replicated to produce the duplexed parvovirus genome DNA of the invention. For the purpose of vector production, the template may be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like. Alternatively, the template may be stably incorporated into the chromosome of a packaging cell.

As used herein, the term "polypeptide" can encompass both peptides and proteins.

As used herein, "transduction, "transfection," or "infection" of a cell by AAV means that the AAV enters the cell to establish a latent or active (i.e., lytic) infection, respectively. See, e.g., Bernard N. Fields et al., Virology, vol. 2, ch. 69 (3d ed., Lippincott-Raven Publishers).

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "stringent conditions" refers to conditions under which a probe will hybridize preferentially to its target subsequence, and to a lesser extent to, or not at all to, other sequences. Put another way, the term "stringent hybridization conditions" as used herein refers to conditions that are compatible to produce duplexes on an array surface between complementary binding members, e.g., between probes and complementary targets in a sample, e.g., duplexes of nucleic acid probes, such as DNA probes, and their corresponding nucleic acid targets that are present in the sample, e.g., their corresponding mRNA analytes present in the sample.

A "stringent hybridization" and "stringent hybridization wash conditions" in the context of nucleic acid hybridization (e.g., as in array, Southern or Northern hybridizations) are sequence dependent, and are different under different environmental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions sets forth the conditions which determine whether a nucleic acid is specifically hybridized to a probe. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403-10. Unless specified otherwise, all sequence identity values provided herein are determined using GCG (Genetics Computer Group, Wisconsin Package, Standard Settings, gap creation penalty 3.0, gap extension penalty 0.1).

Where a range of values is provided, it is understood that each intervening value, to the tenth of the unit of the lower limit unless the context clearly dictates otherwise, between the upper and lower limit of that range and any other stated or intervening value in that stated range, is encompassed within the invention.

All publications and patents cited in this specification are herein incorporated by reference as if each individual publication or patent were specifically and individually indicated to be incorporated by reference.

It is noted that, as used herein and in the appended claims, the singular forms "a", "an", and "the" include pluralities unless the context clearly dictates otherwise.

Stabilized, Parvoviral Vectors and Templates

Stabilized, parvoviral vectors and their templates are provided and, in many embodiments, the parvoviruses are adeno associated viruses. The unique and key improvement is the replacement of one of the two ITRs in the template with a heterologous ITR having less than 90% complementarily to the other ITR.

The genetic stability of the novel "stabilized, double-stranded" (sds) and "stabilized single-stranded" (sss) parvoviral vectors taught herein is substantially increased over conventional parvoviral vectors. The stabilized vectors can, for example, (1) be packaged as efficiently as conventional ssAAV vectors and yield identical high particle titers; and (2) be packaged as dsAAV vectors that contain only the desired ds vector genome—the novel sdsAAV vectors do not suffer contamination problems with ss intermediates resulting from ITR repair as observed with the conventional dsAAV vectors. Moreover, the sdsAAV vectors maintain all the other advantages of the dsAAV approach including, but not limited to, a very rapid and efficient transduction of cells in vitro and in vivo.

Furthermore, the stabilized vectors taught herein also provide for the stable insertion of extremely small (down to 0.2 kb) lengths of foreign DNA, such as recombinant gene expression cassettes between the two ITRs, in a plasmid, for example. As a result, it is now possible to generate recombinant sdsAAV vectors containing, in some embodiments, only an RNAi expression cassette in the absence of any stuffer DNA sequences. Such an RNAi expression cassette may contain, for example, a U6 promoter and an shRNA, typically having a length of ~0.5 kb. Stabilized, double- or single-stranded vectors can be produced in this manner. In some embodiments, for example, the equivalent vectors, sssAAV (stabilized single-stranded), can also stably accommodate inserts as small as 0.2 kb (versus>2.5 for standard ssAAV). It should be noted, however, that in order to assure packaging of a monomer sssAAV genome, it is often beneficial to use inserts no smaller than 2 kb.

Figure 1B:
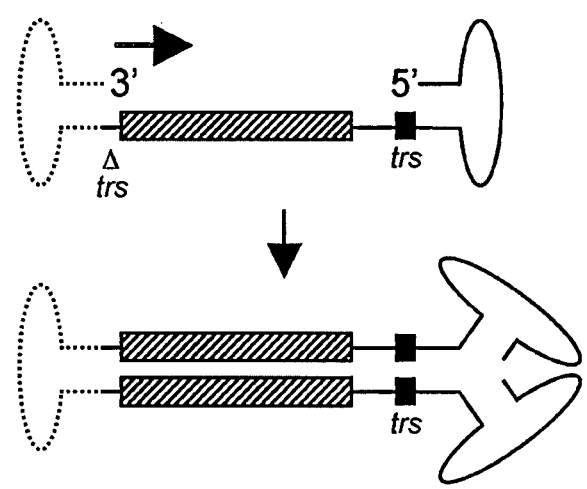

FIGS. 1A-1C illustrate an improved design of double-stranded vector genomes according to some embodiments. FIG. 1A shows the conventional structure of scAAV vectors. An AAV vector genome is shown and contains a transgene expression cassette (hatched box) flanked by the two ITRs in hairpin configuration with two trs sites. During AAV vector particle production, the genome is replicated to give a dimer of the scAAV that becomes packaged in the AAV capsid. However, due to the presence of trs sites at both ends of the genome, this dimer form can be resolved to yield two monomer 'conventional' forms (not shown), which can also become packaged. FIG. 1B shows the improved vector design, wherein the respective ITR is replaced with a largely heterologous sequence too prevent resolution of one end of the vector genome. In this example, the ITR still assumes a hairpin configuration and serves as a primer for DNA replication but does not contain the trs element. Consequently, the DNA replication results in dimer forms that become packaged as scAAV genomes into the AAV capsid. FIG. 1C shows the BssHII fragment (SEQ ID NO:01) derived from the AAV-4 ITR, which is only about 75% homologous to the AAV-2 ITR (mismatched bases are shown in bold and underlined). This fragment furthermore lacks the trs site and is suitable for use in combination with an intact AAV-2 ITR to generate the stabilized, scAAV vector genomes.

The process for creating a stabilized parvovirus vector begins with creating a parvovirus vector genome template nucleic acid. The template nucleic acid includes a 5' inverted terminal repeat (ITR) and a 3' ITR, each flanking an end of a foreign DNA domain. The nucleotide sequence of either the 5' ITR or 3'ITR is a heterologous ITR having a sequence that is less than 90% complementary to the other ITR sequence to prevent ITR repair or conversion and create the stabilized parvovirus vector. As a result, the stabilized parvovirus vector produced using the template nucleic acid is more stable than it would have been if created without the presence of the heterologous ITR in the template nucleic acid.

In some embodiments, the foreign DNA can range, for example, from about 0.2 to about 5.2 kb in length. In some embodiments, the foreign DNA can range from about 0.2 to about 4.5 kb in length, from about 0.25 to about 4.0 kb in length, from about 0.3 to about 3.0 kb in length, from about 0.35 to about 2.2 kb in length, or any range therein.

A variety ITR and trs domain combinations can exist in the stabilized, single-stranded nucleic acid templates. In some embodiments, the heterologous ITR and lacks a functional trs domain. In some embodiments, the 5' ITR is the heterologous ITR lacks a functional trs domain. In some embodiments, the 3' ITR is the heterologous ITR and has the functional trs domain. In some embodiments, the 5' ITR is the heterologous ITR has the functional trs domain.

In some embodiments, the ITRs can range in length from about 115 to about 160 kb in length, from about 118 to about 150 kb in length, from about 120 to about 145 kb in length, or any range therein.

Figure 2:
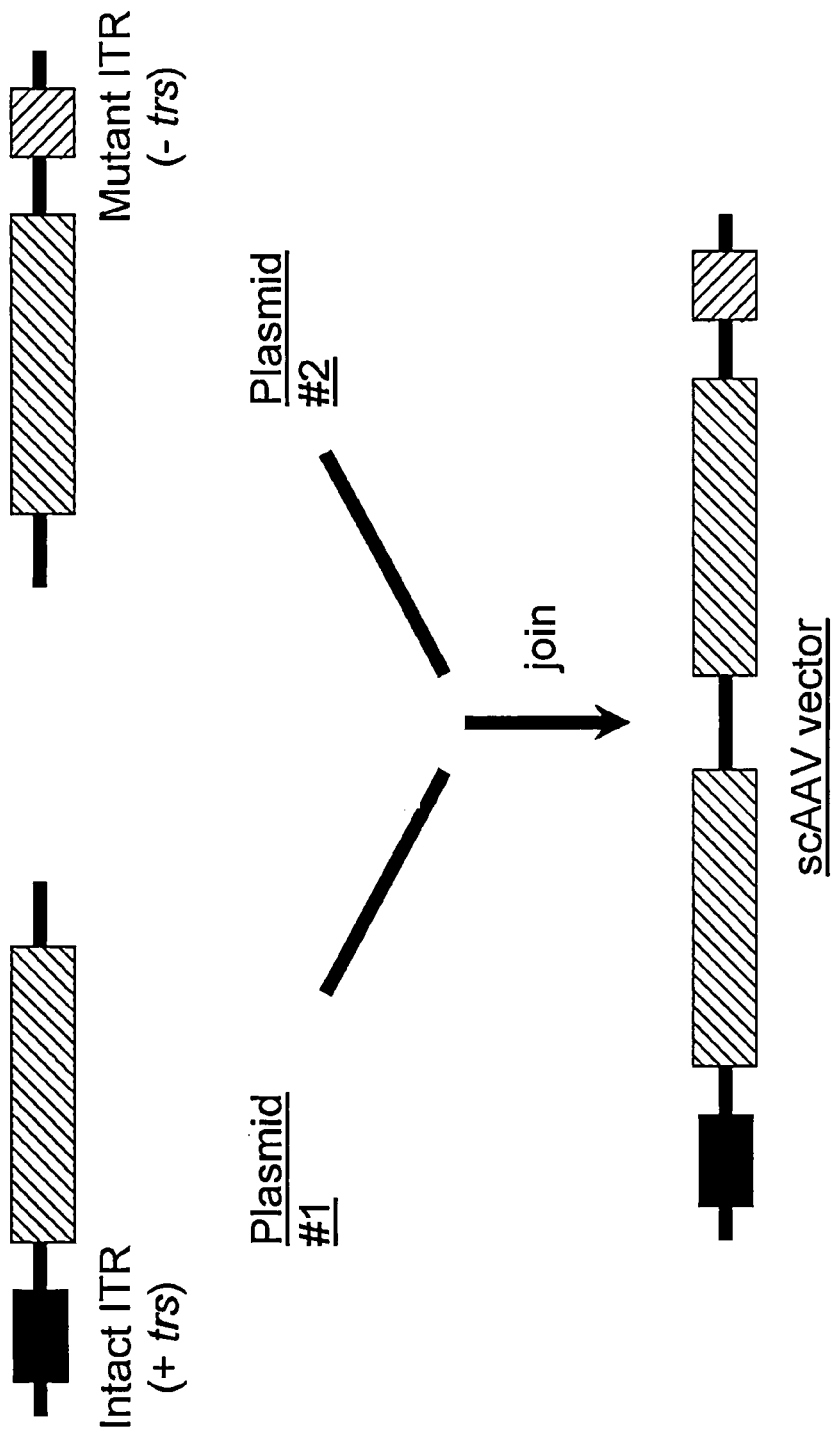
FIG. 2 illustrates a split-plasmid approach for cloning of scAAV vector plasmids according to some embodiments.

The nucleic acid templates may be produced using any method known to those skilled in the art. FIG. 2 illustrates a split-plasmid approach for cloning of scAAV vector plasmids according to some embodiments. To prevent recombination events in the bacterial host, the two ITRs (one intact, and the other lacking the ITR and being heterologous in DNA sequence) are cloned in two separate plasmids. Foreign DNA sequences, e.g. reporter gene or therapeutic gene expression cassettes (hatched boxes), are then cloned into these separate constructs, and as the final step, the two halves are joined to yield a scAAV vector plasmid.

In some embodiments, the vectors are a stabilized, double-stranded parvovirus vector produced by the template nucleic acid. The double-stranded vectors include two inverted copies of a foreign DNA comprising a nucleotide sequence (5'-3') and a complementary (3'-5') nucleotide sequence in a double-stranded configuration; a heterologous inverted terminal repeat (ITR) separating the two inverted copies, wherein the heterologous ITR does not contain a functional terminal resolution site; and, a 5' ITR and a 3' ITR, wherein the 5' ITR and the 3' ITR sequences are substantially complementary to each other to allow for recombination. The heterologous ITR sequence is less than 90% complementary to the 5' ITR and 3' ITR sequences to prevent ITR repair or conversion and create a stabilized parvovirus vector. Accordingly, the stabilized parvovirus vector is more stable than it would have been if created without the presence of the heterologous ITR.

In some embodiments, the phrase "substantially complementary to each other to allow for recombination" can refer to at least 85%, 87%, 88%, 89%, 90%, 92%, 94%, 96%, or 98% complementarity, In some embodiments, the heterologous ITR sequence is less than 90%, 88%, 86%, 84%, 82%, or 80% complementary to the 5' ITR and 3' ITR sequences to prevent ITR repair or conversion and create a stabilized parvovirus vector. Accordingly, the stabilized parvovirus vector is more stable than it would have been if created without the presence of the heterologous ITR.

In some embodiments, the vectors are a stabilized, single-stranded parvovirus vector produced by the template nucleic acid. The single-stranded vector includes a 5' inverted terminal repeat (ITR) and a 3' ITR, each flanking an end of a foreign DNA domain. The nucleotide sequence of either the 5' or 3' ITR is a heterologous ITR having a sequence that is less than 90% complementary to the other ITR sequence to prevent ITR repair or conversion and create a stabilized parvovirus vector. Accordingly, the stabilized parvovirus vector is more stable than it would have been if created without the presence of the heterologous ITR in the template nucleic acid.

In some embodiments, the parvovirus is an adeno-associated virus, where representative adeno-associated viruses (AAV) include, but are not limited to, AAV type 1, AAV type 2, AAV type 3, AAV type 4, AAV type 5, AAV type 6, avian AAV, bovine AAV, canine AAV, equine AAV, and ovine AAV.

In some embodiments, the total length of the vector can be less than 2000 nt, 1900 nt, 1800 nt, 1750 nt, or any amount therein. In some embodiments, the total length of the vector can ranges from about 500 nt to about 1700 nt, from about 800 nt to about 1600 nt, from about 900 nt to about 1200 nt, or any range therein. In some embodiments, the vector may range from about 10% to about 25%, about 20% to about 50%, about 25% to about 40%, about 25% to about 33%, or any range therein, of the wild-type parvovirus genome from which the vector genome was derived.

The 3' ITR and 5' ITR domains can include any naturally occurring parvoviral ITR (or functional synthetic variant thereof). The ITRs can also be a synthetic construct having a hairpin secondary structure. In some embodiments, the ITR is an AAV ITR from any one of the AAV serotypes 1, 2, 3, 4, 5 and 6. The term "ITR" includes synthetic sequences that function as an AAV inverted terminal repeat, such as the "double-D sequence" as described in U.S. Pat. No. 5,478,745, the disclosure of which is hereby incorporated herein in its entirety by reference. In some embodiments, the ITRs do not have a wild-type ITR sequence and may be altered by insertion, deletion, truncation or mutations, as long as the ITR mediates the desired functions, such as virus packaging, integration, provirus rescue, and the like.

In some embodiments, an AAV-2-derived ITRs in an AAV vector plasmid is replaced with an ITR from a heterologous AAV genotype, such as AAV-4. In the ssAAV version, for example, this can be either the left (5') or the right (3') ITR. Likewise, in the dsAAV variant, it can be either the intact or the mutated, trs-deleted ITR. In some embodiments, the heterologous ITR can be chosen from an AAV genotype which differs from AAV-2 (the basis for the other ITR) by at least 10%. In some embodiments, the ITR can be from AAV-4 and differ from the AAV-2 ITR by about 25%.

In some embodiments, the heterologous ITR has less than 80%, 75%, 70%, 65%, 60%, 55%, or 50% complementarity to the other ITR in the template nucleic acid or stabilized, single-stranded parvoviral vector; or to the other two ITRs in the stabilized, double-stranded parvoviral vector. In some embodiments, the heterologous ITR has substantially no complementarity to the other ITR(s).

In many embodiments, the heterologous ITR domain can have a hairpin secondary structure and have less than 90% complementarity to the other ITR in the template nucleic acid or stabilized, single stranded parvoviral vector; or to each of the other two complementary ITRs in the stabilized parvovirus vector. In some embodiments, the 5' ITR and the 3' ITR are less than 75% complementary to the heterologous ITR. In some embodiments, the heterologous ITR lacks a trs domain. In some embodiments, the heterologous ITR has a trs domain. As such, the heterologous ITR can be synthetic, as long as it meets these requirements.

The deletion of the trs domain in most embodiments, regardless of the ITR domain that is mutated, may be limited to the trs site, or may extend 1, 3, 5, 8, 10, 15, 20, 30 nucleotides or more beyond the trs site, as long as the ITR provides for a functional vector. In some embodiments, the 3' ITR lacks a functional trs domain. In some embodiments, the 5' ITR lacks a functional trs domain. In some embodiments, both the 3' ITR and 5' ITR includes a functional trs domain.

In some embodiments, the 3' ITR is a heterologous ITR that cannot recombine with the 5' ITR. In some embodiments, the 5' ITR is a heterologous ITR that cannot recombine with the 3' ITR. In some embodiments, both the 3' ITR and 5' ITR can recombine, and the heterologous ITR separating the inverted copies of the foreign DNA cannot recombine with either the 3' ITR or 5' ITR, thus preventing repair and/or conversion of the heterologous ITR. In some embodiments, the 3' ITR and 5' ITR are substantially complementary to each other to allow for recombination.

The stabilized, double-stranded parvovirus vectors include two inverted copies of a foreign DNA comprising a nucleotide sequence (5'-3') and a complementary (3'-5') nucleotide sequence in a double-stranded configuration. The foreign DNA is generally comprised of DNA that is not naturally occurring in the parvovirus from which the vector is derived. In some embodiments, the foreign DNA can include a viral sequence modified with a promoter that it is not naturally associated with the virus.

In some embodiments, a copy of the foreign DNA can be less than 800 nt, 750 nt, or 700 nt in length. In some embodiments, a copy of the foreign DNA can range in length from about 150 to about 750 nt, from about 200 to about 700 nt, from about 300 to about 600 nt, or any range therein. Each copy of the foreign DNA is substantially complementary to its inverted copy. The term "substantially complementary" can mean that the copies share at least about 85%, about 87%, about 88%, about 90%, about 93%, about 95%, about 98%, or about 99% complementarity, such that the two inverted copies of the foreign DNA may anneal under stringent hybridization conditions to produce double-stranded molecules. In many embodiments, the inverted copies contain an insignificant number of mismatched bases, or even no mismatched bases.

In some embodiments, the foreign DNA includes sense and antisense strands of DNA. In some embodiments, the foreign DNA is in the form of an expression cassette, and include a promoter, an enhancer, and a coding region that encodes an RNAi or a protein. The above regions may be associated with each other in naturally occurring genomic sequences, or may be brought together from other sources using recombinant techniques to provide for a desired performance characteristic of the cassette, such as a strong expression in the host cell, a controllable expression in the host cell, a tissue specific expression, and the like.

The expression cassettes can include nucleic acids encoding therapeutic and/or immunogenic polypeptides. A "therapeutic polypeptide" is a polypeptide that may inhibit, alleviate or reduce symptoms, or prevent a disease. In some embodiments, the disease results from an absence of, or a defect in, a protein in a cell or subject, whether human or veterinary. In some embodiments, the therapeutic effect can include an anti-cancer effect or an improvement in transplant survivability, for example.

In some embodiments, the foreign DNA encodes RNAi including, but not limited to, an shRNA. In these embodiments, the foreign DNA may encode a product in which the RNA agent is a duplex structure of a single ribonucleic acid having a secondary hairpin structure. The length of the duplexed portion of the hairpin structure may vary and, in some embodiments, the length ranges from about 15 bp to about 30 bp, from about 15 bp to about 29 bp, from about 20 bp to about 29 bps, from about 20 bp to about 22 bp, and any range therein.

In some embodiments, the foreign DNA may be in an inverted tandem format to encode other RNAi agents, such as, for example, two single stranded complementary RNA molecules that combine to produce a desired RNAi molecule. In these embodiments, the complementary RNA molecules can be transcribed from opposing promoters, such as described in U.S. Published Application No. 20050060771; which is hereby incorporated herein by reference in its entirety.

In some embodiments, the foreign DNA may encode an antisense nucleic acid; a ribozyme, such as described, for example, in U.S. Pat. No. 5,877,022; RNAs that effect spliceosome-mediated trans-splicing such as described, for example, in U.S. Pat. Nos. 6,013,487 and 6,083,702, and Puttaraju et al., (1999) Nature Biotech. 17: 246; non-translated RNAs, such as the "guide" RNAs taught, for example, in Gorman et al., (1998) Proc. Nat'l Acad. Sci. USA 95: 4929, and U.S. Pat. No. 5,869,248. Each reference of which is hereby incorporated herein by reference in its entirety.

In some embodiments, the foreign DNA may also encode a nucleotide sequence that shares homology with, and recombines with, a locus on the host chromosome to, for example, correct a genetic defect in the host cell.

In some embodiments, the foreign DNA may also include a coding sequence for an immunogenic polypeptide that can be used, for example, in preparing a vaccine. The use of parvoviruses in vaccines is known to those of skill in the art as exemplified, for example, in U.S. Pat. Nos. 5,916,563; 5,905, 040; 5,882,652; and 5,863,541; each of which is hereby incorporated herein by reference it its entirety. In some embodiments, an antigen may be presented in the parvovirus capsid or expressed from an expression cassette introduced into a recombinant vector genome.

The nucleic acid may encode any immunogen known in the art including, but are not limited to, viral antigens, tumor antigens, cancer antigens, bacterial antigens, gag proteins, and the like. In some embodiments, for example, the immunogens are derived from microbial, bacterial, protozoal, parasitic, and viral diseases. In some embodiments, the immunogen may be an orthomyxovirus immunogen such as, for example an influenza virus immunogen including, but not limited to, the influenza virus hemagglutinin (HA) surface protein, the influenza virus nucleoprotein gene, or an equine influenza virus immunogen. In some embodiments, the immunogen may be a lentivirus immunogen such as, for example, an equine infectious anemia virus immunogen, a simian immunodeficiency virus (SIV) immunogen, or a human immunodeficiency virus (HIV) immunogen including, but not limited to, the HIV or SIV envelope GP160 protein, the HIV or SIV matrix/capsid proteins, and the HIV or SIV gag, pol and env gene products.

In some embodiments, the immunogen may also be an arenavirus immunogen such as, for example, a Lassa fever virus immunogen including, but not limited to, the Lassa fever virus nucleocapsid protein gene and the Lassa fever envelope glycoprotein gene. In some embodiments, the immunogen may also be a poxvirus immunogen such as, for example, vaccinia including, but not limited to, the vaccinia L1 or L8 genes. In some embodiments, the immunogen may also be a flavivirus immunogen such as, for example, a yellow fever virus immunogen or a Japanese encephalitis virus immunogen. In some embodiments, the immunogen may also be a filovirus immunogen such as, for example, an Ebola virus immunogen or a Marburg virus immunogen including, but not limited to NP and GP genes.

In some embodiments, the immunogen may also be a bunyavirus immunogen such as, for example, RVFV, CCHF, and SFS viruses. In some embodiments, the immunogen may also be a coronavirus immunogen such as, for example, an infectious human coronavirus immunogen including, but not limited to, the human coronavirus envelope glycoprotein gene, a porcine transmissible gastroenteritis virus immunogen, or an avian infectious bronchitis virus immunogen. In some embodiments, the immunogen may also be a polio immunogen; a herpes antigen including, but not limited to, CAAV, EBV, and HSV immunogens; a mumps immunogen; a measles immunogen; a rubella immunogen; a diptheria toxin or other diptheria immunogen; a pertussis antigen; any hepatitis immunogen including, but not limited to, hepatitis A or B; or any other vaccine immunogen known in the art.

In some embodiments, the immunogen may be any tumor or cancer cell antigen, where the tumor or cancer antigen can be expressed on the surface of the cancer cell. Exemplary cancer and tumor cell antigens are described in S. A. Rosenberg, (1999) Immunity, 10: 281. In some embodiments, the tumor antigens include, but are not limited to, BRCA1 and BRCA2 gene products, GP100, tyrosinase, GAGE-1/2, BAGE, RAGE, NY-ESO-1, CDK-4, catenin, MUM-1, Caspase-8, KIAA0205, HPVE, SART-1, PRAME, P15, and melanoma tumor antigens. See Kawakami et al., (1994) Proc. Natl. Acad. Sci. USA 91: 3515; Kawakami et al., (1994) J. Exp. Med., 180: 347; Kawakami et al., (1994) Cancer Res. 54: 3124.

In some embodiments, the tumor antigens include, but are not limited to, MART-1 (Coulie et al., (1991) J. Exp. Med. 180: 35), GP100 (Wick et al., (1988) J. Cutan. Pathol. 4: 201) and MAGE antigens MAGE-1, MAGE-2 and MAGE-3 (Van der Bruggen et al., (1991) Science, 254: 1643). In some embodiments, the tumor antigens include, but are not limited to, CEA, TRP-1, TRP-2, P-15 and tyrosinase (Brichard et al., (1993) J. Exp. Med. 178: 489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, and p53 tumor suppressor protein (Levine, (1993) Ann. Rev. Biochem. 62: 623).

In some embodiments, the tumor antigens include, but are not limited to, mucin antigens, such as those taught in WO 90/05142; telomerases; nuclear matrix proteins; prostatic acid phosphatase; and papilloma virus antigens. In some embodiments, the tumor antigens include, but are not limited to, antigens associated with the following cancers: melanomas, metastases, adenocarcinoma, thymoma, lymphom, sarcoma, lung cancer, liver cancer, colon cancer, non-Hodgkins lymphoma, Hodgkins lymphoma, leukemias, uterine cancer, breast cancer, prostate cancer, ovarian cancer, cervical cancer, bladder cancer, kidney cancer, and pancreatic cancer. See, for example, Rosenberg, (1996) Ann. Rev. Med. 47: 481-91.

The foreign DNA includes coding sequences operably associated with appropriate control sequences including, but not limited to, expression control elements, such as transcription/translation control signals, origins of replication, polyadenylation signals, and internal ribosome entry sites (IRES), promoters, enhancers, and the like.

A variety of promoter/enhancer elements may be used, and the selection of the promoter/enhancer element depends on the level and tissue-specific expression desired, as well as whether the element will function in the target cell(s). The promoter/enhancer element may be constitutive or inducible, depending on the pattern of expression desired; native and/or foreign; natural and/or synthetic; and, in some embodiments, the element may be mammalian. A native promoter/enhancer is one that is native to the target cell or subject to be treated such that, in some embodiments, the native promoter/enhancer is native to the coding sequence or element of the expression cassette. In a foreign promoter enhancer, for example, the transcriptional initiation region is not found in the wild-type host into which the transcriptional initiation region is introduced.

Inducible expression control elements may be desirable in those applications in which it is desirable to provide regulation over expression of the coding sequence(s). Inducible promoter/enhancer elements for gene delivery may be tissue-specific promoter/enhancer elements, and include muscle specific (including cardiac, skeletal and/or smooth muscle), neural tissue specific (including brain-specific), liver specific, bone marrow specific, pancreatic specific, spleen specific, retinal specific, and lung specific promoter/enhancer elements. In some embodiments, the inducible promoter/enhancer elements include hormone-inducible and metal-inducible elements. In some embodiments, the inducible expression promoter/enhancer elements include, but are not limited to, a Tet on/off element, a RU486-inducible promoter, an ecdysone-inducible promoter, a rapamycin-inducible promoter, and a metalothionein promoter.

In some embodiments, the heterologous nucleic acid sequence(s) will be transcribed and then translated in the target cells. In these embodiments, specific initiation signals are generally required for efficient translation of inserted protein coding sequences. These exogenous translational control sequences, which may include the ATG initiation codon and adjacent sequences, can be of a variety of origins, both natural and synthetic.

Parvoviral Vectors

The stabilized, parvoviral vectors can be administered as an encapsidate particle, or virion. The viral capsid of the subject particles may be from any parvovirus, either an autonomous parvovirus or dependovirus, as described above. In certain embodiments, the viral capsid is an AAV capsid, e.g., AAV1, AAV2, AAV3, AAV4, AAV5 or AAV6 capsid). In many embodiments, the AAV1 capsid, AAV5 capsid, and AAV3 capsid are employed. The choice of parvovirus capsid may be based on a number of considerations as known in the art, such as the target cell type, the desired level of expression, the nature of the heterologous nucleotide sequence to be expressed, issues related to viral production, and the like. For example, the AAV1 capsid may be advantageously employed for skeletal muscle, liver and cells of the central nervous system, such as cells of the brain); AAV5 for cells in the airway and lung; AAV3 for bone marrow cells; and AAV4 for particular cells in the brain, such as appendable cells. In some embodiments, the particles may include two or more copies of a vector genome, e.g., 3 or more, 4 or more, 5 or more, etc., depending on the size of the vector genome.

The parvovirus particle may be a "hybrid" particle in which the viral TRs and viral capsid are from different parvoviruses. In certain embodiments, the viral TRs and capsid are from different serotypes of AAV. Likewise, the parvovirus may have a "chimeric" capsid, such as a capsid containing sequences from different parvoviruses; or a "targeted" capsid, such as a capsid with a directed tropism as described in these publications. See WO 00/28004, U.S. Provisional Application No. 60/248,920; and Chao et al., (2000) Molecular Therapy 2: 619; each of which is hereby incorporated herein in its entirety by reference.

The virions can be produced using any method known to one of skill in the art, such as by introducing the template to be replicated and packaged into a permissive or packaging cell, where a "permissive" cell can be infected or transduced by the virus; and a "packaging" cell is a stably transformed cell providing helper functions. In some embodiments, the method includes a triple-transfection: introducing the nucleic acid templates taught herein into a cell that permits parvovirus replication; introducing an AAV helper plasmid to provide rep and cap genes; introducing an adenoviral helper plasmid to provide helpervirus function; and maintaining the cell under conditions sufficient to produce the stabilized, parvoviral vector, package the vector in a parvovirus capsid, and produce the virion.

The template nucleic acid may be provided in any convenient form including, but not limited to, a plasmid, naked DNA vector, bacterial artificial chromosome, yeast artificial chromosome, or a viral vector. The viral vectors can include an adenovirus, herpesvirus, Epstein-Barr Virus, AAV, baculoviral, retroviral vectors, and the like. Alternatively, the template may be stably incorporated into the genome of a packaging cell. In many embodiments, the parvovirus replication and/or capsid coding sequences are AAV sequences.

Any method of introducing the nucleotide sequence carrying the template into a cellular host for replication and packaging may be used. These methods include, but are not limited to, electoporation, calcium phosphate precipitation, microinjection, and use of cationic or anionic liposomes, as well as liposomes in combination with a nuclear localization signal. Standard methods for producing viral infection may be used in embodiments where the template is provided by a virus vector.

In some embodiments, the template may contain some or all of the parvovirus (e.g., AAV) cap and rep genes. In some embodiments, some or all of the cap and rep functions are provided in trans by introducing a packaging vector(s) encoding the capsid and/or rep proteins into the cell. In certain embodiments, however, the template does not encode the capsid or rep proteins. Alternatively, a packaging cell line can be used that is stably transformed to express the cap and/or rep genes, as described in Gao et al., (1998) Human Gene Therapy 9:2353; Inoue et al., (1998) J. Virol. 72: 7024; U.S. Pat. Nos. 5,837,484 and 5,658,785; WO 98/27207; and WO 96/17947; each of which is hereby incorporated herein in its entirety by reference. Any suitable permissive or packaging cell known in the art can be used to produce the duplexed vectors. In some embodiments, mammalian cells can be used. In many embodiments, trans-complementing packaging cell lines are used and provide functions deleted from a replication-defective helper virus. These cells can include 293 cells or other E1a trans-complementing cells.

In addition, helper virus functions may be provided for the vector to propagate new virus particles. Both adenovirus and herpes simplex virus may serve as helper viruses for AAV. See, for example, Bernard N. Fields et al., Virology, vol. 2, ch. 69, (3d ed., Lippincott-Raven Publishers). Exemplary helper viruses include, but are not limited to, Herpes simplex (HSV), varicella zoster, cytomegalovirus, and Epstein-Barr virus. The multiplicity of infection (MOI) and the duration of the infection will depend on the type of virus used and the packaging cell line that is used. Any suitable helper vector may be used, and in some embodiments, the helper vector(s) can be a plasmid as described by Xiao et al. (1998) J. Virology 72: 2224. The vector can be introduced into the packaging cell by any suitable method known in the art. One of skill will appreciate that other viral particle production protocols may be used, and that the examples provided herein are non-limiting.

In sum, the viral template to be replicated and packaged, parvovirus cap genes, appropriate parvovirus rep genes and, in some embodiments, helper functions are provided to a cell. The cell can be a permissive or packaging cell used to produce parvovirus particles carrying the stabilized, parvoviral vector genome. The combined expression of the rep and cap genes encoded by the template, packaging vector(s), and/or the stably transformed packaging cell results in the production of a parvoviral particle. The virions are allowed to assemble within the cell and may be recovered using any method known by those of skill in the art.

Methods of Using the Subject Parvoviral Vectors

In some embodiments, the invention includes a method of introducing a nucleic acid into a cell, and the nucleic acid can be in the form of an expression cassette. In these embodiments, the cell is contacted with a population of parvoviral virions under conditions sufficient to place the nucleic acid carried by the virion inside the cell. Any suitable protocol known to one of skill can be used.

The manner in which the cell is contacted can vary depending on whether the introduction of the nucleic acid into the cell is carried out in vitro or in vivo. In some embodiments, an in vitro introduction can include exposing the cell to the virions by introducing the virions into the culture medium using any suitable protocol known to one of skill. In some embodiments, an in vivo introduction can include administering a suitable preparation of the virions to the organism in which the cell is located using any suitable method of administration known to one of skill. In many embodiments, intravascular methods of administration can be used including, but not limited to, intra-arterial or intravenous administration.

In some embodiments, the method for introducing the template nucleic acid into at least one cell of a multicellular host by administering to the multicellular host an effective amount of the virion containing the nucleic acid so that the nucleic acid is introduced into at least one cell of the multicellular host. In many embodiments, the multicellular host is a mammal.

There are several uses for the introduction or transfer of a nucleic acid into a cell including, but not limited to, the uses taught in U.S. Pat. Nos. 5,989,540; 5,962,313; 5,952,221; 5,858,775; 5,858,351; 5,846,528; 5,843,742; 5,834,182; 5,789,390; 5,780,447; 5,589,377; and 4,797,368; each of which is hereby incorporated herein by reference in its entirety.

Vectors that include an RNAi encoding expression cassette can be used, for example, in drug screening/target validation; large scale functional library screening; silencing single genes; silencing families of genes, such as for example, those involved in the production of ser/thr kinases, phosphatases, membrane receptors, etc., and the like. And, there are several therapeutic applications involving these concepts, as well as others known to one of skill.

One representative utility of the present invention is as a method of identifying gene function in an organism, especially higher eukaryotes, using the product siRNA to inhibit the activity of a target gene of previously unknown function. Instead of the time consuming and laborious isolation of mutants by traditional genetic screening, functional genomics using vectors delivering RNAi can be used to determine the function of uncharacterized genes. The method includes delivering the RNAi to reduce the amount and/or alter the timing of target gene activity. Vectors delivering RNAi can be used in determining potential targets for pharmaceutics, understanding normal and pathological events associated with tissue development, determining signaling pathways responsible for postnatal development/aging, and the like. The increasing speed of acquiring nucleotide sequence information can be coupled with vectors that deliver RNAi to determine gene function in a cell or in a whole organism and define putative open reading frames.

Vectors delivering RNAi can be used in high-throughput screening. For example, individual clones from a library of clones can be replicated and isolated in separate reactions, or the library can be maintained in individual reaction vessels, such as a 96 well microtiter plate, to minimize the number of steps required and allow automation of the process. Solutions containing the vectors delivering the RNAi and inhibiting the different expressed genes can be placed into individual wells positioned on a microtiter plate as an ordered array, and intact cells/organisms in each well can be assayed for any changes or modifications in behavior or development due to inhibition of target gene activity.

Vectors delivering RNAi can be administered to the cell/organism containing the target gene using any convenient protocol, where the protocol may be an in vitro or in vivo protocol, depending on whether the target cells are in vitro or in vivo. Delivery protocols of interest include the AAV delivery protocols disclosed in: U.S. Pat. Nos. 5,989,540; 5,962,313; 5,952,221; 5,858,775; 5,858,351; 5,846,528; 5,843,742; 5,834,182; 5,789,390; 5,780,447; 5,589,377; 4,797,368; the disclosures of which are herein incorporated by reference.

The function of the target gene can be identified by the effects it has on the cell or organism when the activity of the gene is inhibited. Gene inhibition assays can be processed in large number such as, for example, using tissue culture cells derived from invertebrates or invertebrates, and mammals including primates and humans. If a characteristic of an organism is determined to be genetically linked to a polymorphism through RFLP or QTL analysis, the constructs taught herein can be used to determine whether that genetic polymorphism may be responsible for the characteristic. In some embodiments, a fragment defining the polymorphism, or sequences in the vicinity of such the polymorphism, can be screened using methods can include, but are not limited to, producing an siRNA molecule corresponding to the fragment and evaluating whether an alteration in the characteristic can be correlated with inhibition.

In some embodiments, the constructs can be useful in the inhibition of essential genes. Such genes may be required for cell or organism viability at only particular stages of development or cellular compartments. The functional equivalent of conditional mutations may be produced by inhibiting activity of the target gene when or where it is not required for viability. In some embodiments, siRNA can be administered at specific times of development and locations in the organism without introducing permanent mutations into the target genome.

In situations where alternative splicing produces a family of transcripts that are distinguished by usage of characteristic exons, the present invention can target inhibition through the appropriate exons to specifically inhibit or to distinguish among the functions of family members. For example, a hormone that contained an alternatively spliced transmembrane domain may be expressed in both membrane-bound and secreted forms. Instead of isolating a non-sense mutation that terminates translation before the transmembrane domain, the functional consequences of having only secreted hormone can be determined according to the invention by targeting the exon containing the transmembrane domain and thereby inhibiting expression of membrane-bound hormone.

The RNAi delivery vectors of embodiments of the invention can be used in a variety of therapeutic applications to selectively modulate, for example, one or more target genes in a host including, but not limited to, a whole mammal, or portion thereof, such as a tissue, organ, or individual cells. In such embodiments, an effective amount of a delivery vector can be administered to the host, where the effective amount can be a dosage sufficient to selectively modulate expression of the target gene(s). In some embodiments, the expression of one or more target genes can be inhibited to achieve a desired therapeutic outcome.

Depending on the nature of the condition being treated, the target gene may be a gene derived from the cell, an endogenous gene, a pathologically mutated gene, e.g. a cancer causing gene, one or more genes whose expression causes or is related to heart disease, lung disease, Alzheimer's disease, Parkinson's disease, diabetes, arthritis, etc.; a transgene, or a gene of a pathogen which is present in the cell after infection thereof, e.g., a viral (e.g., HIV-Human Immunodeficiency Virus; HBV-Hepatitis B virus; HCV-Hepatitis C virus; Herpes-simplex 1 and 2; Varicella Zoster (Chicken pox and Shingles); Rhinovirus (common cold and flu); any other viral form) or bacterial pathogen. Depending on the particular target gene and the dose of construct or siRNA product delivered, the procedure may provide partial or complete loss of function for the target gene. Lower doses of injected material and longer times after administration of siRNA may result in inhibition in a smaller fraction of cells.

Embodiments of the methods find use in the treatment of a variety of different conditions in which the modulation of target gene expression in a mammalian host is desired. The term "treatment" can include amelioration of the symptoms associated with a condition, such as a reduction in the severity of a symptom associated with the condition being treated;

inhibition of a pathological condition, or at least symptoms associated therewith, such that the condition may even be completely inhibited, for example, prevented from happening or stopped, such that the host no longer suffers from the condition, or at least the symptoms that characterize the condition.

A variety of hosts can be treated using the constructs taught herein. Such hosts can be "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

The present invention is not limited to modulation of expression of any specific type of target gene or nucleotide sequence. Classes of target genes of interest include but are not limited to: developmental genes (e.g., adhesion molecules, cyclin kinase inhibitors, cytokines/lymphokines and their receptors, growth/differentiation factors and their receptors, neurotransmitters and their receptors); oncogenes (e.g., ABL1, BCL1, BCL2, BCL6, CBFA2, CBL, CSFIR, ERBA, ERBB, EBRB2, ETS1, ETS1, ETV6, FOR, FOS, FYN, HCR, HRAS, JUN, KRAS, LCK, LYN, MDM2, MLL, MYB, MYC, MYCL1, MYCN, NRAS, PIM 1, PML, RET, SRC, TAL1, TCL3, and YES); tumor suppressor genes (e.g., APC, BRCA 1, BRCA2, MADH4, MCC, NF 1, NF2, RB 1, TP53, and WT1); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, Upases, lipoxygenases, lyso/ymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases); chemokines (e.g. CXCR4, CCR5), the RNA component of telomerase, vascular endothelial growth factor (VEGF), VEGF receptor, tumor necrosis factors nuclear factor kappa B, transcription factors, cell adhesion molecules, insulin-like growth factor, transforming growth factor beta family members, cell surface receptors, RNA binding proteins (e.g. small nucleolar RNAs, RNA transport factors), translation factors, telomerase reverse transcriptase); etc.

The uses of interest can include, but are not limited to, those described in U.S. Pat. Nos. 6,547,099; 6,506,559; and 4,766,072; Published U.S. Application No. 20020006664; 20030153519; 20030139363; and published PCT applications of WO 01/68836 and WO 03/010180, each of which are hereby incorporated herein by reference in their entirety.

Virion Preparations

Virion preparations can be used to administer the constructs taught herein. The viral particles or virions in the preparations include the parvoviral vector genomes taught herein, as described above. In some embodiments, substantially all of the virions are stabilized, double-stranded parvoviral vectors. By substantially all is meant at least about 50%, about 60%, about 75%, or any range therein. The virion preparations may also include one or more additional components. In some embodiments, the preparations include a pharmaceutical delivery vehicle. Delivery vehicles of interest include intravascular delivery vehicles, such as water for injection, saline, and the like.

Kits

Also provided are kits for use in preparing the subject vectors and virion preparations, as well as using the prepared virion preparations to introduce a nucleic acid, e.g., functional expression cassette, into a cell. The subject kits include at least elements for producing a population viral particles, as described supra. The elements for producing the population of viral particles may vary depending on the particular vector preparation protocol to be employed, but in certain embodiments will include a plasmid vector that includes a template of the subject vectors (as described above) or component parts or precursors thereof, e.g., first and second plasmids that can be used to produce a template nucleic acid according to the "split-plasmid" approach, as described above. The virion production elements may also include a source of Rep and/or Cap proteins, e.g., a plasmid vector that encodes these proteins (i.e. an AAV packaging plasmid). In addition, the subject elements may include a source of adenovirus helper proteins, e.g. adenovirus, a plasmid containing genes encoding the requisite adenovirus helper proteins (i.e. an adenovirus helper plasmid), and the like. In addition, the kits may include an appropriate packaging cell line, e.g. 293 cell line, HeLa and the like, as well as the packaging cell lines described in U.S. Pat. Nos. 5,872,005; 5,837,484; 5,756,283; 5,691,176; and in vitro analogues thereof as described in U.S. Pat. No. 5,688,676; the disclosures of which are herein incorporated by reference.

The various components of the kit may be present in separate containers or certain compatible components may be precombined into a single container, as desired. In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g. a piece or pieces of paper on which the information is printed, in the packaging of the kit, in a package insert, etc. Yet another means would be a computer readable medium, e.g. diskette, CD, etc., on which the information has been recorded. Yet another means that may be present is a website address which may be used via the internet to access the information at a removed site. Any convenient means may be present in the kits.

The following examples are offered by way of illustration and not by way of limitation.

Example 1

Strategy for scAAV Vector Particle Generation

The following protocol for self-complementary adeno-associated virus (scAAV) vector particle generation provides preparations solely containing packaged dimer molecules. The prototype of scAAV vector genome is modified by replacing one of the two DNA replication/packaging signals (ITRs) flanking the genome with a truncated version with little or no homology to the other ITR (FIG. 1B). This truncated ITR no longer contains the 6 bp trs element, which during replication of the wild-type viral genome is nicked, resulting in formation of monomer DNA forms (FIG. 1B). Moreover, the use of two ITRs with minimal DNA sequence homology minimizes the risk of gene conversion between the intact and the truncated ITR, which could otherwise result in restoration of the trs site at both ends. Heterologous AAV ITRs can either be derived from naturally occurring serotypes of AAV, which differ in DNA sequence, for instance AAV serotypes 2 and 4. Intact AAV-2 ITRs are commonly used in conventional AAV vector constructs and are thus readily available, while a useful restriction enzyme for isolating a minimal ITR from AAV-4 is BssHII, which leaves a trs-deleted 85 bp fragment with only 75% homology to the AAV-2 counterpart (FIG. 1C). Alternatively, a heterologous ITR can be chemically synthesized de novo, but then must be tested for its ability to allow genome excision from the plasmid backbone during particle production. Independent of the origin of the truncated ITR, it may be beneficial to keep the 20 basepair D-sequence found adjacent to the trs in the context of the AAV wildtype genome, as this sequence plays an important role in AAV genome replication and packaging. For instance, the D sequence can be chemically synthesized and cloned into the appropriate position, i.e. next to the truncated ITR, within the scAAV vector genome.

AAV vector particle production can be achieved using a triple-transfection procedure, where cells permissive for AAV replication and packaging (e.g., human kidney 293 cells) are co-transfected with the following plasmids: the AAV vector plasmid (containing the stabilized vector template), the AAV helper plasmid (providing rep and cap), and an adenoviral helper plasmid (providing helpervirus functions). The typical method for triple-transfection is a calcium phosphate-based transfection. The three plasmid are usually transfected in equimolar ratios, using for instance 25 μg of each plasmid per about $2 \times 10^7$ 293 cells (maintained in one 225 cm$^2$ cell culture flask). A typical vector preparation comprises 50×225 cm$^2$ cell culture flasks, containing a total of about $1 \times 10^9$ 293 cells. This requires about 1.25 mg of each of the three plasmids.

The cells are typically incubated for about 2 to 3 days and then harvested. The media is removed (the AAV vector particles remain mostly in the cells, because the virus does not lyse the cells) and the cells are resuspended in a small volume of lysis buffer. For instance, cells from 50 flasks can be resuspended in about 30 ml of lysis buffer. The details of this buffer, as well as of the procedure to actively lyse the cells, and to subsequently purify and titrate the AAV vector particles can vary. See Grimm et al., 2002, Methods, 146-157.

Example 2

Preparation of Small Self-Complementary AAV Vector Genomes

A small self-complementary AAV vector genome was generated that included a shRNA expression cassette of approximately 650 basepairs in size. In DNA extracted from cells transfected with this vector construct and plasmids providing AAV and Adenovirus helper functions, the expected replicative intermediates were detected, confirming that despite its significantly reduced size, the small AAV vector genome replicated correctly.

Figure 3:
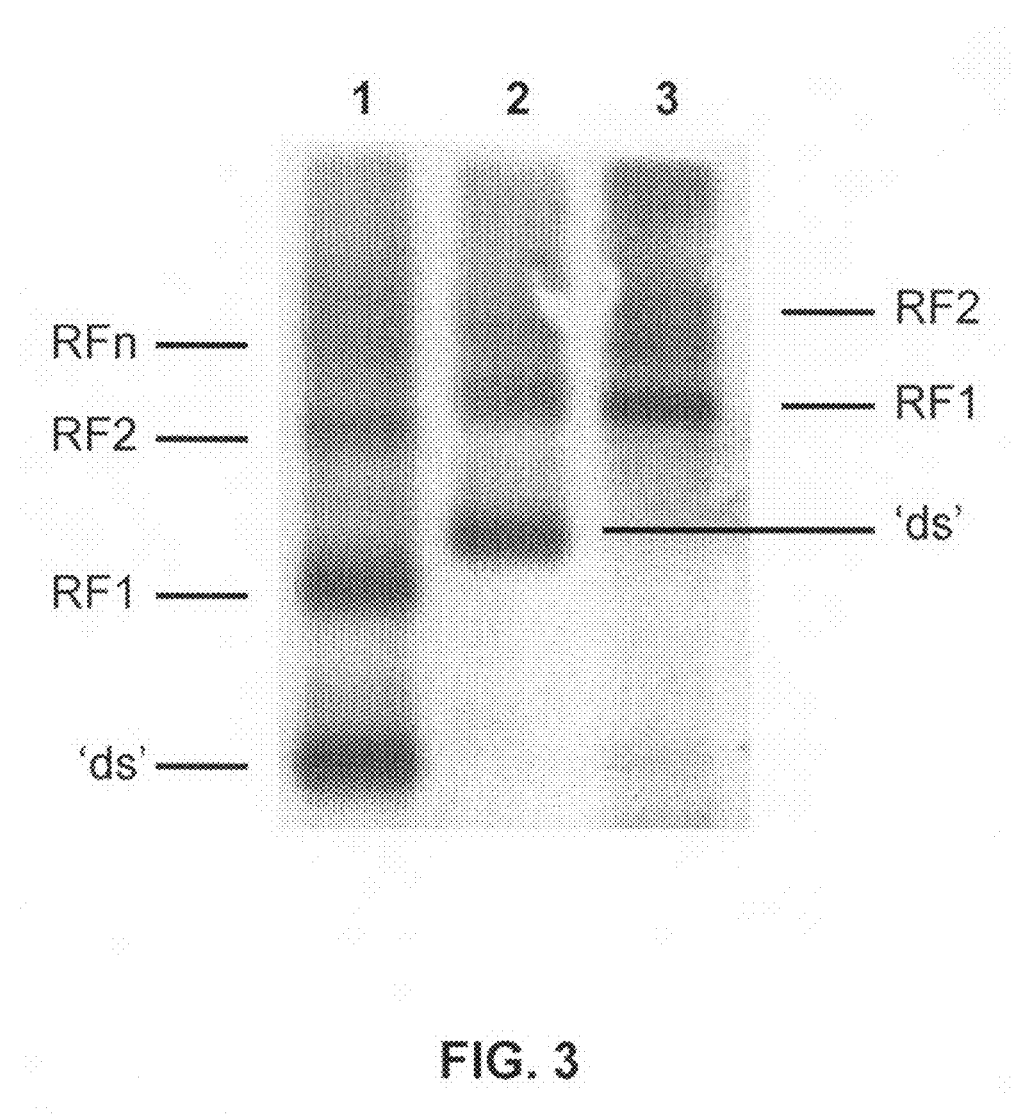
FIG. 3 illustrates extrachromosomally replicated DNA according to some embodiments.

FIG. 3 illustrates extrachromosomally replicated DNA according to some embodiments. The DNA was extracted from cells transfected with a small self-complementary vector genome (lane 1), an approximately 3-fold larger also self-complementary vector (lane 2), and a standard AAV vector construct (lane 3). Note that all cells were also transfected with AAV and Adenovirus helper plasmids. The typical replicative intermediates RF1 and RF2, as well as 'double-stranded' DNA forms, were only observed for the self-complementary vectors.

Example 3

Preparation of Virion Particles Containing AAV Vector Genomes

Figure 4:
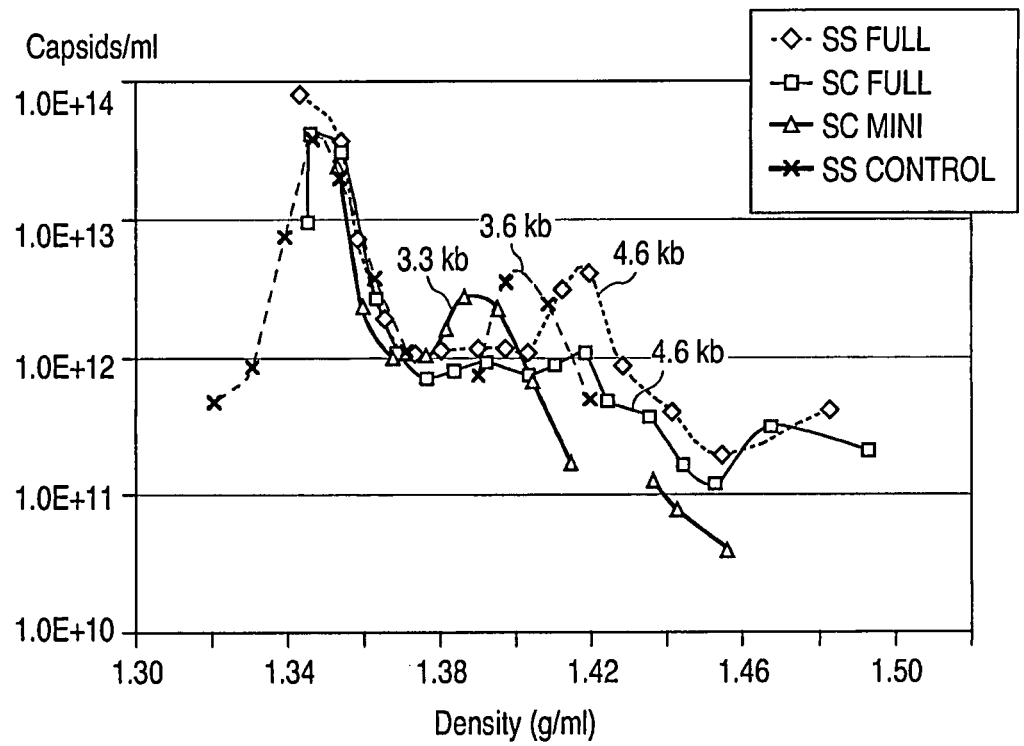
FIG. 4 illustrates formation of virions and their associated capsid density profiles in a CsCl gradient according to some embodiments.

FIG. 4 illustrates formation of virions and their associated capsid density profiles in a CsCl gradient according to some embodiments. The numbers of AAV capsids found in CsCl gradient fractions and their densities (g/ml) are provided. The capsids were obtained through the separate packaging of a small self-complementary vector in ('sc mini length'), a 3-fold larger version ('sc full length'), and two standard AAV vectors of 3.6 ('ss control (gfp)') and 4.6 ('ss full length') kilobases. Peaks of full capsids are highlighted by the numbers, representing the total length of vector DNA encapsidated (3.3 kb for the described small vector).

AAV vector genomes were packaged into AAV-2 capsids, and the resulting particles were fractionated by CsCl gradient density centrifugation and analysed for total capsid numbers by A20 Elisa (Grimm et al., Gene Ther., (1999) 6:1322-1330. A peak of full capsids was observed that was slightly shifted to fractions with lighter density, as compared to the peak found for particles containing a 3.6 kb standard AAV genome. There was successful packaging of two copies of the small self-complementary vector genome, together comprising approximately 3.3 kb (two tandems of the shRNA cassette, plus linker and flanking packaging signals).

Example 4 hFIX Expression Cassette and Plasmid Administered to Mice

An hFIX vector was prepared for administration into mice. FIG. 5 illustrates the sequence for the hFIX expression cassette. The sequence for the hFIX expression cassette (SEQ ID NO:2) includes an enhancer/promoter and the hFIX gene with an intron and poly A signal, and the capital letters designate the hFIX gene itself, according to some embodiments. The plasmid containing the hFIX expression cassette, pNEB193-SynEnh-TTR-hFIX1090-spA (SEQ ID NO:3) has the following full-length sequence:

```
                                        (SEQ ID NO:3)
tcgcgcgtttcggtgatgacggtgaaaacctctgacacatgcagctcccg gagacggtcacagcttgtctgtaagcggatgccgggagcagacaagcccg tcagggcgcgtcagcgggtgttggcgggtgtcggggctggcttaactatg cggcatcagagcagattgtactgagagtgcaccatatgcggtgtgaaata ccgcacagatgcgtaaggagaaaataccgcatcaggcgccattcgccatt caggctgcgcaactgttgggaagggcgatcggtgcgggcctcttcgctat tacgccagctggcgaaaggggatgtgctgcaaggcgattaagttgggta acgccaggttttcccagtcacgacgttgtaaaacgacggccagtgaatt cgagctcggtacccggggcgcgccggatctgtcaattcacgcgagttaa taattaccagcgcgggccaaataaataatcgcgagggggcaggtgacgttt gcccagcgcgcgctggtaattattaaccctcgcgaatattgattcgaggcc
```

-continued gcgattgccgcaatcgcgaggggcaggtgacctttgcccagcgcgcgttc
gccccgccccgacggtatcgatgtcgaggggatccactgggaggatg
ttgagtaagatggaaaactactgatgacccttgcagagacagagtattag
gacatgtttgaacaggggccgggcgatcagcaggtagctctagaggtacc
ccagatctagtgtctgtctgcacatttcgtagagcgagtgttccgatact
ctaatctccctaggcaaggttcatatttgtgtaggttacttattctcctt
ttgttgactaagtcaataatcagaatcagcaggtttggagtcagcttggc
agggatcagcagcctgggttggaaggaggggggtataaaagcccccttcacc
aggagaagcccagctgggcgcgccggatccttaattaaATGCAGCGCGTG
AACATGATCATGGCAGAATCACCAGGCCTCATCACCATCTGCCTTTTAGG
ATATCTACTCAGTGCTGAATGTACAggtttgtttcattaaaaacaaagac
tttcttaagagatgtaaaattttcatgatgttttcttttttgctaaaact
aaagaattattcttttacatttcaGTTTTTCTTGATCATGAAAACGCCAA
CAAAATTCTGAATCGGCCAAAGAGGTATAATTCAGGTAAATTGGAAGAGT
TTGTTCAAGGGAACCTTGAGAGAGAATGTATGGAAGAAAAGTGTAGTTTT
GAAGAAGCACGAGAAGTTTTTGAAAACACTGAAAGAACAACTGAATTTTG
GAAGCAGTATGTTGATGGAGATCAGTGTGAGTCCAATCCATGTTTAAATG
GCGGCAGTTGCAAGGATGACATTAATTCCTATGAATGTTGGTGTCCCTTT
GGATTTGAAGGAAAGAACTGTGAATTAGATGTAACATGTAACATTAAGAA
TGGCAGATGCGAGCAGTTTTGTAAAAATAGTGCTGATAACAAGGTGGTTT
GCTCCTGTACTGAGGGATATCGACTTGCAGAAAACCAGAAGTCCTGTGAA
CCAGCAGTGCCATTTCCATGTGGAAGAGTTTCTGTTTCACAAACTTCTAA
GCTCACCCGTGCTGAGGCTGTTTTCCTGATGTGGACTATGTAAATTCTA
CTGAAGCTGAAACCATTTTGGATAACATCACTCAAAGCACCCAATCATTT
AATGACTTCACGCGTGTTGTTGGTGGAGAAGATGCCAAACCAGGTCAATT
CCCTTGGCAGGTTGTTTTGAATGGTAAAGTTGATGCATTCTGTGGAGGCT
CTATCGTTAATGAAAATGGATTGTAACTGCTGCCCACTGTGTTGAAACT
GGTGTTAAAATTACAGTTGTCGCCGGCGAACATAATATTGAGGAGACAGA
ACATACAGAGCAAAAGCGAAATGTGATTCGAATTATTCCTCACCACAACT
ACAATGCAGCTATTAATAAGTACAACCATGACATTGCCCTTCTGGAACTG
GACGAACCCTTAGTGCTAAACAGCTACGTTACACCTATTTGCATTGCTGA
CAAGGAATACACGAACATCTTCCTCAAATTTGGATCTGGCTATGTAAGTG
GCTGGGAAGAGTCTTCCACAAAGGGAGATCAGCTTTAGTTCTTCAGTAC
CTTAGAGTTCCACTTGTTGACCGAGCCACATGTCTTCGATCTACAAAGTT
CACCATCTATAACAACATGTTCTGTGCTGGCTTCCATGAAGGAGGTAGAG
ATTCATGTCAAGGAGATAGTGGGGACCCCATGTTACTGAAGTGGAAGGG
ACCAGTTTCTTAACTGGAATTATTAGCTGGGGTGAAGAGTGTGCAATGAA
AGGCAAATATGGAATATATACCAAGGTATCCCGGTATGTCAACTGGATTA
AGGAAAAACAAAGCTCACTTAATtaagtctagagtcgacctagaactag
taataaaggatcctttattttcattggatccgtgtgttggttttttgtgt -continued gcggccgcgtcgagtcgactgtttaaacctgcaggcatgcaagcttggcg
taatcatggtcatagctgtttcctgtgtgaaattgttatccgctcacaat
tccacacaacatacgagccggaagcataaagtgtaaagcctggggtgcct
aatgagtgagctaactcacattaattgcgttgcgctcactgcccgctttc
cagtcgggaaacctgtcgtgccagctgcattaatgaatcggccaacgcgc
ggggagaggcggtttgcgtattgggcgctcttccgcttcctcgctcactg
actcgctgcgctcggtcgttcggctgcggcgagcggtatcagctcactca
aaggcggtaatacggttatccacagaatcaggggataacgcaggaaagaa
catgtgagcaaaaggccagcaaaaggccaggaaccgtaaaaaggccgcgt
tgctggcgtttttccataggctccgcccccctgacgagcatcacaaaaat
cgacgctcaagtcagaggtggcgaaacccgacaggactataaagatacca
ggcgtttccccctggaagctccctcgtgcgctctcctgttccgaccctgc
cgcttaccggatacctgtccgcctttctcccttcgggaagcgtggcgctt
tctcatagctcacgctgtaggtatctcagttcggtgtaggtcgttcgctc
caagctgggctgtgtgcacgaaccccccgttcagcccgaccgctgcgcct
tatccggtaactatcgtcttgagtccaacccggtaagacacgacttatcg
ccactggcagcagccactggtaacaggattagcagagcgaggtatgtagg
cggtgctacagagttcttgaagtggtggcctaactacggctacactagaa
ggacagtatttggtatctgcgctctgctgaagccagttaccttcggaaaa
agagttggtagctcttgatccggcaaacaaaccaccgctggtagcggtgg
ttttttttgtttgcaagcagcagattacgcgcagaaaaaaaggatctcaag
aagatcctttgatcttttctacggggtctgacgctcagtggaacgaaaac
tcacgttaagggattttggtcatgagattatcaaaaaggatcttcaccta
gatccttttaaattaaaaatgaagttttaaatcaatctaaagtatatatg
agtaaacttggtctgacagttaccaatgcttaatcagtgaggcacctatc
tcagcgatctgtctatttcgttcatccatagttgcctgactccccgtcgt
gtagataactacgatacgggagggcttaccatctggccccagtgctgcaa
tgataccgcgagacccacgctcaccggctccagatttatcagcaataaac
cagccagccggaagggccgagcgcagaagtggtcctgcaactttatccgc
ctccatccagtctattaattgttgccgggaagctagagtaagtagttcgc
cagttaatagtttgcgcaacgttgttgccattgctacaggcatcgtggtg
tcacgctcgtcgtttggtatggcttcattcagctccggttcccaacgatc
aaggcgagttacatgatcccccatgttgtgcaaaaaagcggttagctcct
tcggtcctccgatcgttgtcagaagtaagttggccgcagtgttatcactc
atggttatggcagcactgcataattctcttactgtcatgccatccgtaag
atgcttttctgtgactggtgagtactcaaccaagtcattctgagaatagt
gtatgcggcgaccgagttgctcttgcccggcgtcaatacgggataatacc
gcgccacatagcagaactttaaaagtgctcatcattggaaaacgttcttc
ggggcgaaaactctcaaggatcttaccgctgttgagatccagttcgatgt
aacccactcgtgcacccaactgatcttcagcatcttttactttcaccagc
gtttctgggtgagcaaaaacaggaaggcaaaatgccgcaaaaaagggaat -continued aagggcgacacggaaatgttgaatactcatactcttccttttcaatatt attgaagcatttatcagggttattgtctcatgagcggatacatatttgaa tgtatttagaaaaataaacaaatagggggttccgcgcacatttccccgaaa agtgccacctgacgtctaagaaaccattattatcatgacattaacctata aaaataggcgtatcacgaggccctttcgtc Hemophilia B, or factor IX deficiency, is an X-linked recessive disorder occurring in about 1 in 25,000 males. Affected individuals are at risk for spontaneous bleeding into many organs; treatment mainly consists of the transfusion of clotting factor concentrates prepared from human blood or recombinant sources after bleeding has started.

Figure 6:
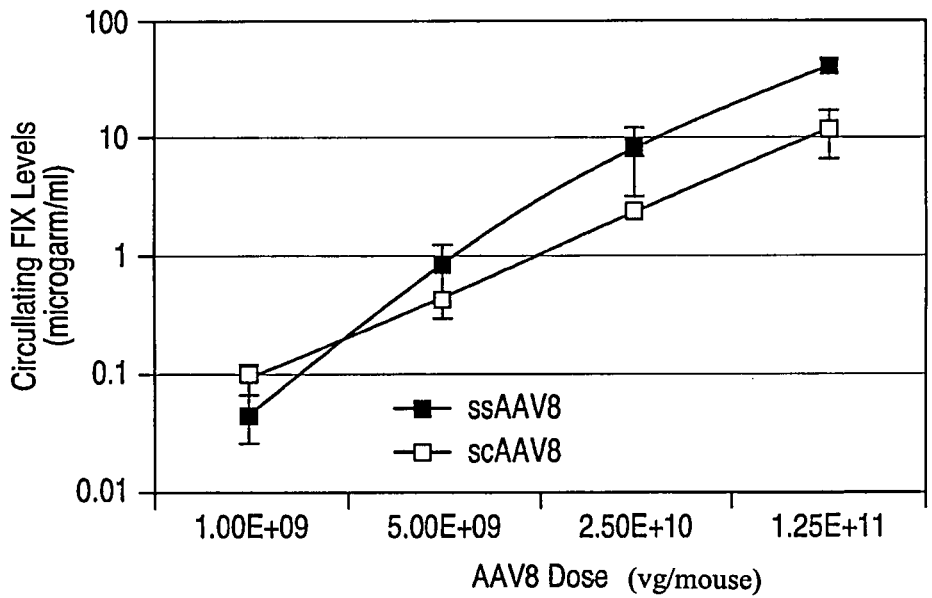
FIG. 6 illustrates the effectiveness of sds and sss AAV-8 hFIX vectors in mice according to some embodiments.

Small- and large-animal models have been developed and/or characterized that closely mimic the human disease state. As a preclinical model for gene therapy, recombinant adeno-associated viral vectors containing the human or canine factor IX cDNAs were infused into the livers of mouse and dog models of hemophilia B, respectively. FIG. 6 illustrates the effectiveness of sds and sss AAV-8 hFIX vectors in mice according to some embodiments. Both sds and sss AAV-8 hFIX vectors have been shown to be therapeutically useful as a means to increase circulating FIX levels. Note that the increase in FIX level for administration of the single-stranded vector over the double-stranded vector at a given dose is due to the use of a weaker promoter in the sdsAAV.

Figure 7:
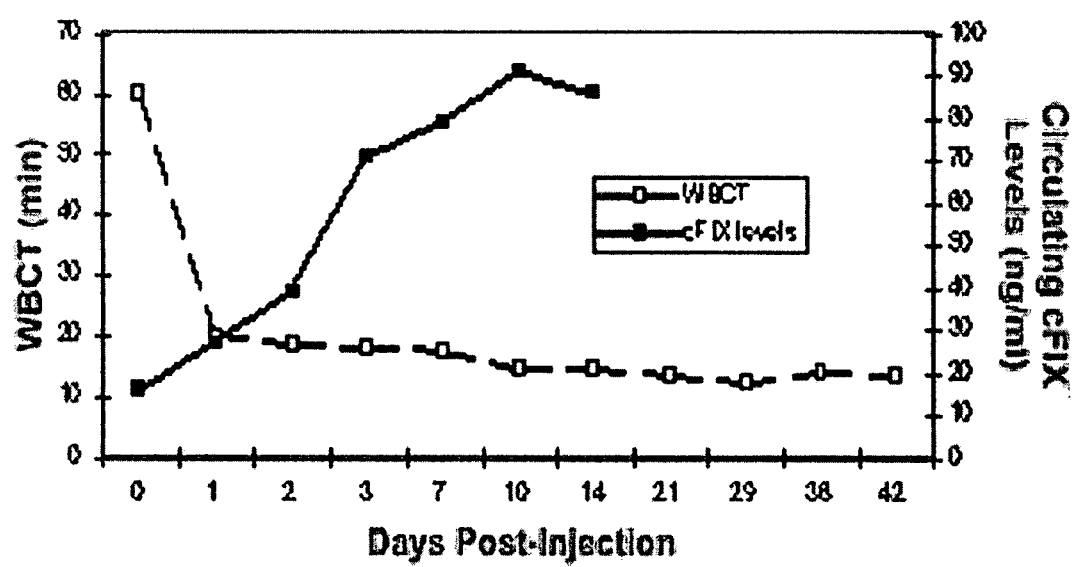
FIG. 7 illustrates the effectiveness of sds AAV-8 cFIX vectors in dogs according to some embodiments.

FIG. 7 illustrates the effectiveness of sds AAV-8 cFIX vectors in dogs according to some embodiments. In the sds vector AAV-8, the hFIX was substituted for cFIX, and the vector was administered to dogs. Whole blood clotting time (WBCT) in minutes and the relative circulating cFIX levels in ng/ml were measured and plotted against the number of days following injection. The relationships provided in FIG. 7 shows that administration of the sds AAV-8 cFIX vector is therapeutically useful to induce clotting in dogs.

Example 5

Stability of the Stabilized, Double-Stranded AAV Vector

The increased stability of the sds AAV vectors have been observed using restriction enzyme digests on conventional dsAAV vectors (both intact and deleted ITR from AAV-2) as compared to the stabilized plasmids that include the heterologous ITR. The plasmids shown in this example contain an shRNA expression cassette.

Figure 8:
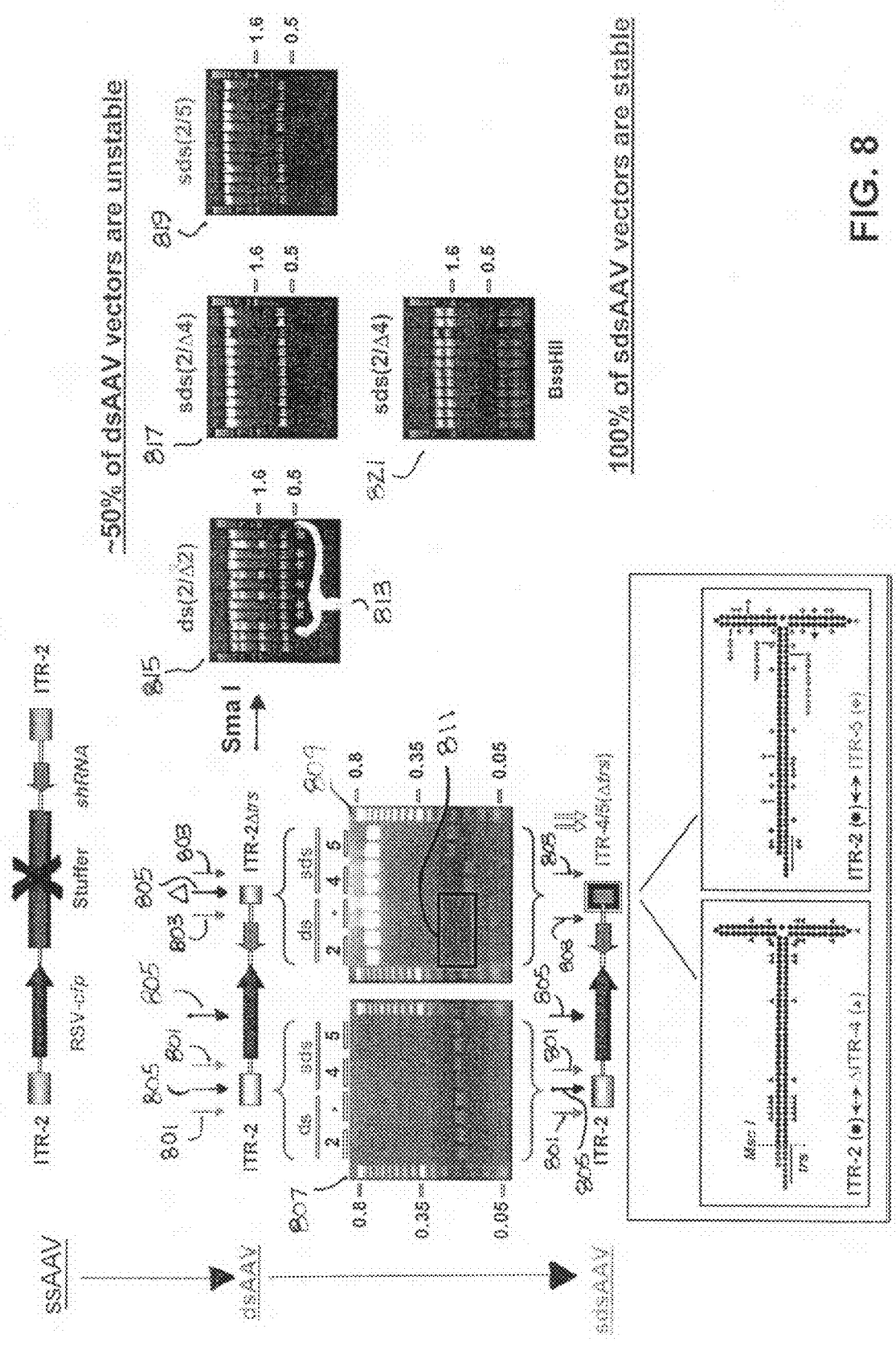
FIG. 8 illustrates the increased stability of the stabilized, double-stranded vectors according to some embodiments.

FIG. 8 illustrates the increased stability of the stabilized, double-stranded vectors according to some embodiments. The arrows at 801 indicate the use of Pst I restriction enzyme. The arrows at 803 indicate the use of BssH II restriction enzyme, and the arrows at 805 indicate the use of Sma I restriction enzyme. The procedure was performed on randomly selected individual bacterial colonies after transformation of the plasmids.

The two gels on the left of FIGS. 8, 807 and 809, show that in about 50% of all plasmids having the conventional design (without the heterologous ITR), the mutated ITR was completely lost due to recombination/deletion events, where the box indicated by 811 in gel 809 points out the deleted clones. The other gels confirm this, by showing more clones. Sma I cuts in the AAV-2 ITR, and one can see that a characteristic band is missing in .about.50% of all clones with the conventional design, where the asterisks indicated by 813 in gel 815 also point out the deleted clones. In contrast, 100% of the stabilized clones are genetically stable, as confirmed also by Sma I as well as by BssH II digests (for the AAV-4 ITR vector) as seen in gels 817, 819, and 821.

One of skill will understand that the teachings herein have very broad applications and a wide variety of foreign DNA can be delivered using, for example, any of a variety of promoters. In some embodiments, shRNAs can be expressed from a human U6 promoter. In some embodiments, shRNAs can be expressed from a human H1 promoter. In some embodiments, to facilitate shRNA cloning, an sdsAAV vector can be designed to contain a U6 promoter followed by a unique Bbs I restriction enzyme site, allowing insertion of shRNAs as annealed oligonucleotides with appropriate overhangs. In some embodiments, the hairpins can be designed such that the sense comes before the antisense strand, separated by a 7-9 nucleotide loop.

The following Table includes shRNA that has been used to produce the stabilized, parvoviral vectors. The column labeled 'Target' provides the genes targeted by the respective shRNAs such as, for example, Hepatitis C Virus (HCV), and fatty acid transporter protein (FATP). As referenced to the mouse genome, the term "NONE" indicates there is no such gene target in the mouse genome. The column labeled "shRNA" provides the respective name of shRNA with a particular stem length in nucleotides ("Stem"). The columns labeled "Sense" and "Antisense" provides the respective DNA strands, where the underlined nucleotides are mismatches between the strands. The column labeled "Loop" provides the respective loop sequences ranging in length from 7 to 9 nucleotides, where "A" is 5' TCAAGAG 3', "B" is 5' GAAGCTTG 3', and "C" is 5' TTCAAGAGA 3'.

| Target | shRNA | Stem | Sense (5'-3') | Antisense (5'-3') | Loop | SEQ ID NO: (Sense) | SEQ ID NO: (Antisense) |
|---|---|---|---|---|---|---|---|
| hAAT | hAAT-19 | 19 | GAAGCGTTTAGGCATGTTT | AAACATGCCTAAACGCTTC | A | 4 | 5 |
|  | hAAT-21 | 21 | GAAGCGTTTAGGCATGTTTAA | TTAAACATGCCTAAACGCTTC | A | 6 | 7 |
|  | hAAT-23 | 23 | GAAGCGTTTAGGCATGTTTAACA | TGTTAAACATGCCTAAACGCTTC | A | 8 | 9 |
|  | hAAT-25 | 25 | GAAGCGTTTAGGCATGTTTAACATC | GATGTTAAACATGCCTAAACGCTTC | A | 10 | 11 |
|  | A-25 | 25 | GAAGCGTTTAGGCATGTTTAACATC | GATGTTAAACATGCCTAAACGCTTC | B | 12 | 13 |
|  | R-25 | 25 | GATGTTAAACATGCCTAAACGCTTC | GAAGCGTTTAGGCATGTTTAACATC | A | 14 | 15 |
|  | A-3 | 21 | AAGCGTTTAGGCATGTTTAAC | GTTAAACATGCCTAAACGCTT | A | 16 | 17 |
|  | A-6 | 19 | AAGCGTTTAGGCATGTTTA | TAAACATGCCTAAACGCTT | A | 18 | 19 |
|  | R-19 | 19 | AAACATGCCTAAACGCTTC | GAAGCGTTTAGGCATGTTT | A | 20 | 21 |
| Luc | Luc-19 | 19 | TCCCGCTGAATTGGAATCC | GGATTCCAATTCAGCGGGA | A | 22 | 23 |
|  | Luc-21 | 21 | GCTCCCGCTGAATTGGAATCC | GGATTCCAATTCAGCGGGAGC | A | 24 | 25 |
|  | Luc-23 | 23 | TGGCTCCCGCTGAATTGGAATCC | GGATTCCAATTCAGCGGGAGCCA | A | 26 | 27 |
|  | Luc-25 | 25 | GGTGGCTCCCGCTGAATTGGAATCC | GGATTCCAATTCAGCGGGAGCCACC | A | 28 | 29 |

| Target | shRNA | Stem | Sense (5'-3') | Antisense (5'-3') | Loop | SEQ ID NO: (Sense) | SEQ ID NO: (Antisense) |
|---|---|---|---|---|---|---|---|
| | Luc-29 | 29 | ATCGGGCGGCTCTCGCTGAGTTGGAATCC | GGATTCCAATTCAGCGGGAGCCACCTGAT | B | 30 | 31 |
| | L19.1 | 19 | GGTGGCTCCCGCTGAATTG | CAATTCAGCGGGAGCCACC | A | 32 | 33 |
| | L19.2 | 19 | GCTCCCGCTGAATTGGAAT | ATTCCAATTCAGCGGGAGC | A | 34 | 35 |
| HBsAg | sAg-19 | 19 | TTACTAGTGCCATTTGTTC | GAACAAATGGCACTAGTAA | A | 36 | 37 |
| | sAg-21 | 21 | GTTTACTAGTGCCATTTGTTC | GAACAAATGGCACTAGTAAAC | A | 38 | 39 |
| | sAg-23 | 23 | CAGTTTACTAGTGCCATTTGTTC | GAACAAATGGCACTAGTAAACTG | A | 40 | 41 |
| | sAg-25 | 25 | CTCAGTTTACTAGTGCCATTTGTTC | GAACAAATGGCACTAGTAAACTGAG | A | 42 | 43 |
| | sAg-25' | 25 | CTCGGTTTATTAGTGCCGTTTGTTC | GAACAAATGGCACTAGTAAACTGAG | B | 44 | 45 |
| | FA1 | 25 | CTCAGTTTAGTAGTGCCATTTGTTC | GAACAAATGGCACTAGTAAACTGAG | B | 46 | 47 |
| | FA2 | 25 | CTCGGTTTATTAGTGCCGTTTGTTC | GAACAAACGGCACTAATAAACCGAG | B | 48 | 49 |
| | FA7 | 25 | CTCGGTTTATTAGTGCCGTTTGTTC | GAACAAATGGCACTAGTAAACTGAG | A | 50 | 51 |
| | hbv22 | 19 | GGCTCAGTTTACTAGTGCC | GGCACTAGTAAACTGAGCC | A | 52 | 53 |
| | M3 | 21 | ATTGTGAGGATTCTTGTCAAC | GTTGACAAGAATCCTCACAAT | A | 54 | 55 |
| | M4 | 21 | ATACAGGTGCAATTTCCGTCC | GGACGGAAATTGCACCTGTAT | A | 56 | 57 |
| | M5 | 21 | TGTAACACGAGAAGGGGTCCT | AGGACCCCTTCTCGTGTTACA | A | 58 | 59 |
| | M6 | 21 | ACAAGTTGGAGGACAGGAGGT | ACCTCCTGTCCTCCAACTTGT | A | 60 | 61 |
| | M7 | 21 | TGGTACAGCAACAGGAGGGAT | ATCCCTCCTGTTGCTGTACCA | A | 62 | 63 |
| HBcAg | cAg-19 | 19 | AGAAGAACTCCCTCGCCTC | GAGGCGAGGGAGTTCTTCT | A | 64 | 65 |
| | cAg-21 | 21 | GAAGAAGAACTCCCTCGCCTC | GAGGCGAGGGAGTTCTTCTTC | A | 66 | 67 |
| | cAg-23 | 23 | TAGAAGAAGAACTCCCTCGCCTC | GAGGCGAGGGAGTTCTTCTTCTA | A | 68 | 69 |
| | cAg-25 | 25 | CCTAGAAGAAGAACTCCCTCGCCTC | GAGGCGAGGGAGTTCTTCTTCTAGG | A | 70 | 71 |
| | cAg-25' | 25 | CCTAGGAGAAGGACTCCCTTGCCTC | GAGGCGAGGGAGTTCTTCTTCTAGG | B | 72 | 73 |
| | FA3 | 25 | CCTAGAAGAAGAACTCCCTCGCCTC | GAGGCGAGGGAGTTCTTCTTCTAGG | B | 74 | 75 |
| | FA4 | 25 | CCTAGGAGAAGGACTCCCTTGCCTC | GAGGCAAGGGAGTCCTTCTCCTAGG | B | 76 | 77 |
| | FA5 | 25 | CCTAGGAGAAGGACTCCCTTGCCTC | GAGGCGAGGGAGTTCTTCTTCTAGG | A | 78 | 79 |
| | FA6 | 25 | CCTAGAAGAAGAACTCCCTCGCCTC | GAGGCAAGGGAGTCCTTCTCCTAGG | B | 80 | 81 |
| | K19.1 | 19 | CCTAGAAGAAGAACTCCCT | AGGGAGTTCTTCTTCTAGG | A | 82 | 83 |
| | K19.2 | 19 | GAAGAAGAACTCCCTCGCC | GGCGAGGGAGTTCTTCTTC | A | 84 | 85 |
| HCV | HCV1 | 20 | GCGAAAGGCCTTGTGGTACT | AGTACCACAAGGCCTTTCGC | B | 86 | 87 |
| | HCV2 | 20/21 | GTGCACGGTCTACGAGACCTC | GAGGTCTCGTAGACCGTGCA | B | 88 | 89 |
| | HCV3 | 19 | ATTGGAGTGAGTTTAAGCT | AGCTTAAACTCACTCCAAT | B | 90 | 91 |
| FATP | F2-6 | 19 | GGTATGAGCTGATCAAGTA | TACTTGATCAGCTCATACC | C | 92 | 93 |
| | F2-7 | 19 | GGCGACATCTACTTCAACA | TGTTGAAGTAGATGTCGCC | C | 94 | 95 |
| | F5-2 | 19 | GTGGAAATCTCCTGCCATA | TATGGCAGGAGATTTCCAC | C | 96 | 97 |
| | F5-3 | 19 | GTTCTCTGCCTCCCGATTC | GAATCGGGAGGCAGAGAAC | C | 98 | 99 |
| NONE | SCR | 19 | GATCGAATGTGTACTTCGA | TCGAAGTACACATTCGATC | C | 100 | 101 |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. As will be apparent to those of skill in the art upon reading this disclosure, each of the individual embodiments described and illustrated herein has discrete components and features which may be readily separated from or combined with the features of any of the other several embodiments without departing from the scope or spirit of the teachings.

We claim:

1. A parvovirus vector template nucleic acid for creating a self-complementary, genetically stable, infectious recombinant, adeno-associated virus (rAAV) virion comprising:
   a) a 5' inverted terminal repeat (ITR);
   b) a 3' ITR; and
   c) a foreign DNA insert comprising one or more expression cassettes, each independently ranging in size from about 0.2 kb to about 2.2 kb, and adding up to a total size of no more than 2.4 kb in length between the 5'ITR and the 3' ITR;
   wherein (i) the 5' and the 3' ITR have between 50 and 80% complementarity to each other, (ii) the 3' ITR serves as a primer for DNA replication, (iii) the 5' or 3' ITR is from AAV-2 and the other ITR is from AAV-4, and (iv) at least one of the 5' or 3' ITRs does not contain a functional terminal resolution site (trs).

2. The template nucleic acid of claim 1, wherein the expression cassette includes a promoter, a coding sequence and a termination signal.

3. The template nucleic acid of claim 1, wherein the 5' ITR is from AAV-2 and the 3' ITR is from AAV-4.

4. The template nucleic acid of claim 1, wherein the 5' ITR is from AAV-4 and the 3' ITR is from AAV-2.

5. The template nucleic acid of claim 1, wherein the foreign DNA insert encodes a protein.

6. The template nucleic acid of claim 1, wherein the foreign DNA insert encodes an RNAi product.

7. The template nucleic acid of claim 6, wherein the RNAi product is an shRNA or a micro-RNA.

8. The template nucleic acid of claim 1, wherein the foreign DNA insert comprises more than one expression cassette.

9. A plasmid comprising the template nucleic acid of claim 1.

10. A kit for use in producing an adeno-associated virus (rAAV) virion, said kit comprising:
    a) a plasmid comprising the template nucleic acid of claim 1;
    b) an AAV helper plasmid to provide rep and cap genes;
    c) an adenoviral helper plasmid to provide helpervirus function; and
    d) instructions for producing the adeno-associated virus (rAAV) virion.

11. The template nucleic acid of claim 1, wherein the template nucleic acid is single-stranded.

12. The template nucleic acid of claim 11, wherein the foreign DNA insert encodes an shRNA or a micro-RNA.

13. The template nucleic acid of claim 1, wherein the template nucleic acid is double-stranded.

14. The template nucleic acid of claim 13, wherein the foreign DNA insert encodes an shRNA or a micro-RNA.

15. The template nucleic acid of claim 1, wherein the ITR from AAV-4 consists essentially of the trs-deleted BssHII fragment of SEQ ID NO: 1.

16. A method of producing a self-complementary, genetically stable, infectious recombinant, adeno-associated virus (rAAV) virion, said method comprising:
    a) introducing the nucleic acid of claim 1 into a cell that permits viral replication;
    b) introducing an AAV helper plasmid to provide rep and cap genes;
    c) introducing an adenoviral helper plasmid to provide helper virus function; and
    d) maintaining the cell under conditions sufficient to produce a stabilized, self-complementary double-stranded parvovirus vector, package the vector in a parvovirus capsid, and produce the parvovirus virion.

17. A genetically stable, double-stranded viral genome, comprising:
    a) two inverted copies of a foreign DNA insert; and
    b) first and second ITR sequences having between 50 and 80% complementarity to each other; wherein the first or second ITR serves as a primer for DNA replication but does not contain a functional terminal resolution site; wherein the first or the second ITR is between the two inverted copies of the foreign DNA insert, and wherein the first ITR sequence is from AAV-2 and the second ITR sequence is from AAV-4.

18. The double-stranded viral genome of claim 17, wherein the ITR from AAV-4 consists essentially of the trs-deleted BssHII fragment of SEQ ID NO: 1.

19. A genetically stable, single-stranded viral genome, comprising:
    a) a foreign DNA insert; and
    b) first and second ITR sequences having between 50 and 80% complementarity to each other;
    wherein the first or second ITR serves as a primer for DNA replication but does not contain a functional terminal resolution site, and wherein the first ITR sequence is from AAV-2 and the second ITR sequence is from AAV-4.

20. The single-stranded viral genome of claim 19, wherein the ITR from AAV-4 consists essentially of the trs-deleted BssHII fragment of SEQ ID NO: 1.

21. The viral genome of claim 17 or 19, wherein the foreign DNA insert encodes a protein.

22. The viral genome of claim 17 or 19, wherein the foreign DNA insert encodes an RNAi product.

23. The viral genome of claim 22, wherein the RNAi product is an shRNA or a micro-RNA.

24. A genetically stable, infectious recombinant, adeno-associated virus (rAAV) virion comprising:
    a) a parvovirus capsid; and,
    b) the viral genome of claim 17 or 19.

25. A composition comprising the virion of claim 24 in a pharmaceutically acceptable carrier.

26. An isolated cell comprising the genetically stable, infectious recombinant, adeno-associated virus (rAAV) virion of claim 24.

27. A method for introducing a foreign DNA insert comprising one or more expression cassettes into at least one cell of a mammalian host, the method comprising: administering to the mammalian host an effective amount of the virion of claim 24 so that the foreign DNA insert is introduced into at least one cell of the mammalian host.

28. The method of claim 27, wherein the foreign DNA insert contains an expression cassette encoding Factor IX (FIX) to increase a level of FIX in blood of the mammalian host and induce clotting.

* * * * *

SEQUENCE LISTING

<160> NUMBER OF SEQ ID NOS: 101

<210> SEQ ID NO 1
<211> LENGTH: 85
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 1
cgcgctcgct cactcactcg gccctgccgg ccagaggccg gcagtctgga gacctttggt     60
ctccagggcc gagtgagtga gcgag                                          85

```
<210> SEQ ID NO 2
<211> LENGTH: 2120
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 2
```

| | | | | | |
|---|---|---|---|---|---|
| gagttaataa | ttaccagcgc | gggccaaata | aataatcgcg | aggggcaggt | gacgtttgcc | 60 |
| cagcgcgcgc | tggtaattat | taacctcgcg | aatattgatt | cgaggccgcg | attgccgcaa | 120 |
| tcgcgagggg | caggtgacct | tgcccagcg | cgcgttcgcc | ccgccccgga | cggtatcgat | 180 |
| gtcgaggggg | atcccactgg | gaggatgttg | agtaagatgg | aaaactactg | atgaccccttg | 240 |
| cagagacaga | gtattaggac | atgtttgaac | aggggccggg | cgatcagcag | gtagctctag | 300 |
| aggtaccccca | gatctagtgt | ctgtctgcac | atttcgtaga | gcgagtgttc | cgatactcta | 360 |
| atctccctag | gcaaggttca | tatttgtgta | ggttacttat | tctccttttg | ttgactaagt | 420 |
| caataatcag | aatcagcagg | tttggagtca | gcttggcagg | atcagcagc | ctgggttgga | 480 |
| aggagggggt | ataaaagccc | cttcaccagg | agaagcccag | ctgggcgcgc | cggatcctta | 540 |
| attaaatgca | gcgcgtgaac | atgatcatgg | cagaatcacc | aggcctcatc | accatctgcc | 600 |
| ttttaggata | tctactcagt | gctgaatgta | caggtttgtt | tcattaaaaa | caaagactttt | 660 |
| cttaagagat | gtaaaatttt | catgatgttt | tcttttttgc | taaaactaaa | gaattattct | 720 |
| tttacatttc | agttttttctt | gatcatgaaa | acgccaacaa | aattctgaat | cggccaaaga | 780 |
| ggtataattc | aggtaaattg | gaagagttttg | ttcaagggaa | ccttgagaga | gaatgtatgg | 840 |
| aagaaaagtg | tagtttttgaa | gaagcacgag | aagttttttga | aaacactgaa | agaacaactg | 900 |
| aattttggaa | gcagtatgtt | gatggagatc | agtgtgagtc | caatccatgt | ttaaatggcg | 960 |
| gcagttgcaa | ggatgacatt | aattcctatg | aatgttggtg | tcccttttgga | tttgaaggaa | 1020 |
| agaactgtga | attagatgta | acatgtaaca | ttaagaatgg | cagatgcgag | cagttttgta | 1080 |
| aaaatagtgc | tgataacaag | gtggtttgct | cctgtactga | gggatatcga | cttgcagaaa | 1140 |
| accagaagtc | ctgtgaacca | gcagtgccat | ttccatgtgg | aagagtttct | gttttcacaaa | 1200 |
| cttctaagct | cacccgtgct | gaggctgttt | ttcctgatgt | ggactatgta | aattctactg | 1260 |
| aagctgaaac | catttttggat | aacatcactc | aaagcaccca | atcatttaat | gacttcacgc | 1320 |
| gtgttgttgg | tggagaagat | gccaaaccag | gtcaattccc | ttggcaggtt | gtttttgaatg | 1380 |
| gtaaagttga | tgcattctgt | ggaggctcta | tcgttaatga | aaaatggatt | gtaactgctg | 1440 |
| cccactgtgt | tgaaactggt | gttaaaatta | cagttgtcgc | cggcgaacat | aatattgagg | 1500 |
| agacagaaca | tacagagcaa | aagcgaaatg | tgattcgaat | tattcctcac | cacaactaca | 1560 |
| atgcagctat | taataagtac | aaccatgaca | ttgcccttct | ggaactggac | gaacccttag | 1620 |
| tgctaaacag | ctacgttaca | cctatttgca | ttgctgacaa | ggaatacacg | aacatcttcc | 1680 |
| tcaaatttgg | atctggctat | gtaagtggct | ggggaagagt | cttccacaaa | gggagatcag | 1740 |
| ctttagttct | tcagtaccctt | agagttccac | ttgttgaccg | agccacatgt | cttcgatcta | 1800 |
| caaagttcac | catctataac | aacatgttct | gtgctggctt | ccatgaagga | ggtagagatt | 1860 |
| catgtcaagg | agatagtggg | ggaccccatg | ttactgaagt | ggaagggacc | agtttcttaa | 1920 |
| ctggaattat | tagctggggt | gaagagtgtg | caatgaaagg | caaatatgga | atatatacca | 1980 |
| aggtatcccg | gtatgtcaac | tggattaagg | aaaaaacaaa | gctcacttaa | ttaagtctag | 2040 |
| agtcgaccta | gaactagtaa | taaaggatcc | tttattttca | ttggatccgt | gtgttggttt | 2100 | tttgtgtgcg ccgcgtcga 2120

<210> SEQ ID NO 3
<211> LENGTH: 4830
<212> TYPE: DNA
<213> ORGANISM: Artificial Sequence
<220> FEATURE:
<223> OTHER INFORMATION: Description of Artificial Sequence: Synthetic construct

<400> SEQUENCE: 3

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggc      420
gcgccggatc tgtcaattca cgcgagttaa taattaccag cgcgggccaa ataaataatc     480
gcgaggggca ggtgacgttt gcccagcgcg cgctggtaat tattaacctc gcgaatattg     540
attcgaggcc gcgattgccg caatcgcgag gggcaggtga cctttgccca gcgcgcgttc     600
gccccgcccc ggacggtatc gatgtcgagg gggatcccac tgggaggatg ttgagtaaga     660
tggaaaacta ctgatgaccc ttgcagagac agagtattag gacatgtttg aacaggggcc     720
gggcgatcag caggtagctc tagaggtacc ccagatctag tgtctgtctg cacatttcgt     780
agagcgagtg ttccgatact ctaatctccc taggcaaggt tcatatttgt gtaggttact     840
tattctcctt ttgttgacta agtcaataat cagaatcagc aggtttggag tcagcttggc     900
agggatcagc agcctgggtt ggaaggaggg ggtataaaag ccccttcacc aggagaagcc     960
cagctgggcg cgccggatcc ttaattaaat gcagcgcgtg aacatgatca tggcagaatc    1020
accaggcctc atcaccatct gccttttagg atatctactc agtgctgaat gtacaggttt    1080
gtttcattaa aaacaaagac tttcttaaga gatgtaaaat tttcatgatg ttttcttttt    1140
tgctaaaact aaagaattat tcttttacat ttcagttttt cttgatcatg aaaacgccaa    1200
caaaattctg aatcggccaa agaggtataa ttcaggtaaa ttggaagagt tgttcaagg     1260
gaaccttgag agagaatgta tggaagaaaa gtgtagtttt gaagaagcac gagaagtttt    1320
tgaaaacact gaaagaacaa ctgaattttg gaagcagtat gttgatggag atcagtgtga    1380
gtccaatcca tgtttaaatg gcggcagttg caaggatgac attaattcct atgaatgttg    1440
gtgtcccttt ggatttgaag gaaagaactg tgaattagat gtaacatgta acattaagaa    1500
tggcagatgc gagcagtttt gtaaaaatag tgctgataac aaggtggttt gctcctgtac    1560
tgagggatat cgacttgcag aaaaccagaa gtcctgtgaa ccagcagtgc catttccatg    1620
tggaagagtt tctgtttcac aaacttctaa gctcacccgt gctgaggctg ttttttcctga   1680
tgtggactat gtaaattcta ctgaagctga aaccattttg gataacatca ctcaaagcac    1740
ccaatcattt aatgacttca cgcgtgttgt tggtggagaa gatgccaaac caggtcaatt    1800
cccttggcag gttgttttga atggtaaagt tgatgcattc tgtggaggct ctatcgttaa    1860
tgaaaaatgg attgtaactg ctgccactg tgttgaaact ggtgttaaaa ttacagttgt    1920
cgccggcgaa cataatattg aggagacaga acatacagag caaaagcgaa atgtgattcg    1980
```

```
aattattcct caccacaact acaatgcagc tattaataag tacaaccatg acattgccct    2040
tctggaactg gacgaaccct tagtgctaaa cagctacgtt acacctattt gcattgctga    2100
caaggaatac acgaacatct tcctcaaatt tggatctggc tatgtaagtg gctggggaag    2160
agtcttccac aaagggagat cagctttagt tcttcagtac cttagagttc cacttgttga    2220
ccgagccaca tgtcttcgat ctacaaagtt caccatctat aacaacatgt tctgtgctgg    2280
cttccatgaa ggaggtagag attcatgtca aggagatagt gggggacccc atgttactga    2340
agtggaaggg accagtttct taactggaat tattagctgg ggtgaagagt gtgcaatgaa    2400
aggcaaatat ggaatatata ccaaggtatc ccggtatgtc aactggatta aggaaaaaac    2460
aaagctcact taattaagtc tagagtcgac ctagaactag taataaagga tcctttattt    2520
tcattggatc cgtgtgttgg ttttttgtgt gcggccgcgt cgagtcgact gtttaaacct    2580
gcaggcatgc aagcttggcg taatcatggt catagctgtt tcctgtgtga aattgttatc    2640
cgctcacaat tccacacaac atacgagccg gaagcataaa gtgtaaagcc tggggtgcct    2700
aatgagtgag ctaactcaca ttaattgcgt tgcgctcact gcccgctttc cagtcgggaa    2760
acctgtcgtg ccagctgcat taatgaatcg gccaacgcgc ggggagaggc ggtttgcgta    2820
ttgggcgctc ttccgcttcc tcgctcactg actcgctgcg ctcggtcgtt cggctgcggc    2880
gagcggtatc agctcactca aaggcggtaa tacggttatc cacagaatca ggggataacg    2940
caggaaagaa catgtgagca aaaggccagc aaaaggccag gaaccgtaaa aaggccgcgt    3000
tgctggcgtt tttccatagg ctccgccccc ctgacgagca tcacaaaaat cgacgctcaa    3060
gtcagaggtg gcgaaacccg acaggactat aaagatacca ggcgtttccc cctggaagct    3120
ccctcgtgcg ctctcctgtt ccgaccctgc cgcttaccgg atacctgtcc gcctttctcc    3180
cttcgggaag cgtggcgctt tctcatagct cacgctgtag gtatctcagt tcggtgtagg    3240
tcgttcgctc caagctgggc tgtgtgcacg aaccccccgt tcagcccgac cgctgcgcct    3300
tatccggtaa ctatcgtctt gagtccaacc cggtaagaca cgacttatcg ccactggcag    3360
cagccactgg taacaggatt agcagagcga ggtatgtagg cggtgctaca gagttcttga    3420
agtggtggcc taactacggc tacactagaa ggacagtatt tggtatctgc gctctgctga    3480
agccagttac cttcggaaaa agagttggta gctcttgatc cggcaaacaa accaccgctg    3540
gtagcggtgg tttttttgtt tgcaagcagc agattacgcg cagaaaaaaa ggatctcaag    3600
aagatccttt gatcttttct acggggtctg acgctcagtg gaacgaaaac tcacgttaag    3660
ggattttggt catgagatta tcaaaaagga tcttcaccta gatccttta aattaaaaat    3720 gaagttttaa atcaatctaa agtatatatg agtaaacttg gtctgacagt taccaatgct    3780
taatcagtga ggcacctatc tcagcgatct gtctatttcg ttcatccata gttgcctgac    3840
tccccgtcgt gtagataact acgatacggg agggcttacc atctggcccc agtgctgcaa    3900
tgataccgcg agacccacgc tcaccggctc cagatttatc agcaataaac cagccagccg    3960
gaagggccga gcgcagaagt ggtcctgcaa ctttatccgc ctccatccag tctattaatt    4020
gttgccggga agctagagta agtagttcgc cagttaatag tttgcgcaac gttgttgcca    4080
ttgctacagg catcgtggtg tcacgctcgt cgtttggtat ggcttcattc agctccggtt    4140
cccaacgatc aaggcgagtt acatgatccc ccatgttgtg caaaaaagcg gttagctcct    4200
tcggtcctcc gatcgttgtc agaagtaagt tggccgcagt gttatcactc atggttatgg    4260
cagcactgca taattctctt actgtcatgc catccgtaag atgcttttct gtgactggtg    4320
```

```
agtactcaac caagtcattc tgagaatagt gtatgcggcg accgagttgc tcttgcccgg    4380
cgtcaatacg ggataatacc gcgccacata gcagaacttt aaaagtgctc atcattggaa    4440
aacgttcttc ggggcgaaaa ctctcaagga tcttaccgct gttgagatcc agttcgatgt    4500
aacccactcg tgcacccaac tgatcttcag catcttttac tttcaccagc gtttctgggt    4560
gagcaaaaac aggaaggcaa aatgccgcaa aaagggaat aagggcgaca cggaaatgtt    4620
gaatactcat actcttcctt tttcaatatt attgaagcat ttatcagggt tattgtctca    4680
tgagcggata catatttgaa tgtatttaga aaaataaaca aatagggggtt ccgcgcacat    4740 ttccccgaaa agtgccacct gacgtctaag aaaccattat tatcatgaca ttaacctata    4800
aaaataggcg tatcacgagg ccctttcgtc                                    4830
```

```
<210> SEQ ID NO 4
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 4
gaagcgttta ggcatgttt                                                  19

<210> SEQ ID NO 5
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 5
aaacatgcct aaacgcttc                                                  19

<210> SEQ ID NO 6
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 6
gaagcgttta ggcatgttta a                                               21

<210> SEQ ID NO 7
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 7
ttaaacatgc ctaaacgctt c                                               21

<210> SEQ ID NO 8
<211> LENGTH: 23
<212> TYPE: DNA
<213> ORGANISM: Unknown Organism
<220> FEATURE:
<223> OTHER INFORMATION: Description of Unknown Organism: shRNA sequence

<400> SEQUENCE: 8
gaagcgttta ggcatgttta aca                                             23
```

```
<210> SEQ ID NO 9
<211> LENGTH: 23
<212> TYPE: DNA
<213> ORGANISM: Unknown Organism
<220> FEATURE:
<223> OTHER INFORMATION: Description of Unknown Organism: shRNA sequence

<400> SEQUENCE: 9
tgttaaacat gcctaaacgc ttc                                              23

<210> SEQ ID NO 10
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 10
gaagcgttta ggcatgttta acatc                                            25

<210> SEQ ID NO 11
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 11
gatgttaaac atgcctaaac gcttc                                            25

<210> SEQ ID NO 12
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 12
gaagcgttta ggcatgttta acatc                                            25

<210> SEQ ID NO 13
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 13
gatgttaaac atgcctaaac gcttc                                            25

<210> SEQ ID NO 14
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 14
gatgttaaac atgcctaaac gcttc                                            25

<210> SEQ ID NO 15
<211> LENGTH: 25
<212> TYPE: DNA
<213> ORGANISM: Unknown Organism
<220> FEATURE:
<223> OTHER INFORMATION: Description of Unknown Organism: shRNA sequence
```

<400> SEQUENCE: 15
gaagcgttta ggcatgttta acatc     25

<210> SEQ ID NO 16
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 16
aagcgtttag gcatgtttaa c     21

<210> SEQ ID NO 17
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 17
gttaaacatg cctaaacgct t     21

<210> SEQ ID NO 18
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 18
aagcgtttag gcatgttta     19

<210> SEQ ID NO 19
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 19
taaacatgcc taaacgctt     19

<210> SEQ ID NO 20
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 20
aaacatgcct aaacgcttc     19

<210> SEQ ID NO 21
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 21
gaagcgttta ggcatgttt     19

<210> SEQ ID NO 22
<211> LENGTH: 19

-continued

```
<212> TYPE: DNA
<213> ORGANISM: Unknown Organism
<220> FEATURE:
<223> OTHER INFORMATION: Description of Unknown Organism: shRNA sequence

<400> SEQUENCE: 22
tcccgctgaa ttggaatcc                                                  19

<210> SEQ ID NO 23
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 23
ggattccaat tcagcggga                                                  19

<210> SEQ ID NO 24
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 24
gctcccgctg aattggaatc c                                               21

<210> SEQ ID NO 25
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 25
ggattccaat tcagcgggag c                                               21

<210> SEQ ID NO 26
<211> LENGTH: 23
<212> TYPE: DNA
<213> ORGANISM: Unknown Organism
<220> FEATURE:
<223> OTHER INFORMATION: Description of Unknown Organism: shRNA sequence

<400> SEQUENCE: 26
tggctcccgc tgaattggaa tcc                                             23

<210> SEQ ID NO 27
<211> LENGTH: 23
<212> TYPE: DNA
<213> ORGANISM: Unknown Organism
<220> FEATURE:
<223> OTHER INFORMATION: Description of Unknown Organism: shRNA sequence

<400> SEQUENCE: 27
ggattccaat tcagcgggag cca                                             23

<210> SEQ ID NO 28
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 28
```

```
ggtggctccc gctgaattgg aatcc                                           25

<210> SEQ ID NO 29
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 29
ggattccaat tcagcgggag ccacc                                           25

<210> SEQ ID NO 30
<211> LENGTH: 29
<212> TYPE: DNA
<213> ORGANISM: Unknown Organism
<220> FEATURE:
<223> OTHER INFORMATION: Description of Unknown Organism: shRNA sequence

<400> SEQUENCE: 30
atcgggcggc tctcgctgag ttggaatcc                                       29

<210> SEQ ID NO 31
<211> LENGTH: 29
<212> TYPE: DNA
<213> ORGANISM: Unknown Organism
<220> FEATURE:
<223> OTHER INFORMATION: Description of Unknown Organism: shRNA sequence

<400> SEQUENCE: 31
ggattccaat tcagcgggag ccacctgat                                       29

<210> SEQ ID NO 32
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 32
ggtggctccc gctgaattg                                                  19

<210> SEQ ID NO 33
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 33
caattcagcg ggagccacc                                                  19

<210> SEQ ID NO 34
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 34
gctcccgctg aattggaat                                                  19

<210> SEQ ID NO 35
<211> LENGTH: 19
<212> TYPE: DNA
<213> ORGANISM: Unknown Organism
```

```
<220> FEATURE:
<223> OTHER INFORMATION: Description of Unknown Organism: shRNA sequence

<400> SEQUENCE: 35
attccaattc agcgggagc                                                    19

<210> SEQ ID NO 36
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 36
ttactagtgc catttgttc                                                    19

<210> SEQ ID NO 37
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 37
gaacaaatgg cactagtaa                                                    19

<210> SEQ ID NO 38
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 38
gtttactagt gccatttgtt c                                                 21

<210> SEQ ID NO 39
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 39
gaacaaatgg cactagtaaa c                                                 21

<210> SEQ ID NO 40
<211> LENGTH: 23
<212> TYPE: DNA
<213> ORGANISM: Unknown Organism
<220> FEATURE:
<223> OTHER INFORMATION: Description of Unknown Organism: shRNA sequence

<400> SEQUENCE: 40
cagtttacta gtgccatttg ttc                                               23

<210> SEQ ID NO 41
<211> LENGTH: 23
<212> TYPE: DNA
<213> ORGANISM: Unknown Organism
<220> FEATURE:
<223> OTHER INFORMATION: Description of Unknown Organism: shRNA sequence

<400> SEQUENCE: 41
gaacaaatgg cactagtaaa ctg                                               23
```

<210> SEQ ID NO 42
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 42
ctcagtttac tagtgccatt tgttc                                       25

<210> SEQ ID NO 43
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 43
gaacaaatgg cactagtaaa ctgag                                       25

<210> SEQ ID NO 44
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 44
ctcggtttat tagtgccgtt tgttc                                       25

<210> SEQ ID NO 45
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 45
gaacaaatgg cactagtaaa ctgag                                       25

<210> SEQ ID NO 46
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 46
ctcagtttac tagtgccatt tgttc                                       25

<210> SEQ ID NO 47
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 47
gaacaaatgg cactagtaaa ctgag                                       25

<210> SEQ ID NO 48
<211> LENGTH: 25
<212> TYPE: DNA
<213> ORGANISM: Unknown Organism
<220> FEATURE:
<223> OTHER INFORMATION: Description of Unknown Organism: shRNA sequence

```
<400> SEQUENCE: 48
ctcggtttat tagtgccgtt tgttc                                            25

<210> SEQ ID NO 49
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 49
gaacaaacgg cactaataaa ccgag                                            25

<210> SEQ ID NO 50
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 50
ctcggtttat tagtgccgtt tgttc                                            25

<210> SEQ ID NO 51
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 51
gaacaaatgg cactagtaaa ctgag                                            25

<210> SEQ ID NO 52
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 52
ggctcagttt actagtgcc                                                   19

<210> SEQ ID NO 53
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 53
ggcactagta aactgagcc                                                   19

<210> SEQ ID NO 54
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 54
attgtgagga ttcttgtcaa c                                                21

<210> SEQ ID NO 55
```

-continued

```
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 55
gttgacaaga atcctcacaa t                                              21

<210> SEQ ID NO 56
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 56
atacaggtgc aatttccgtc c                                              21

<210> SEQ ID NO 57
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 57
ggacggaaat tgcacctgta t                                              21

<210> SEQ ID NO 58
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 58
tgtaacacga gaaggggtcc t                                              21

<210> SEQ ID NO 59
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 59
aggacccctt ctcgtgttac a                                              21

<210> SEQ ID NO 60
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 60
acaagttgga ggacaggagg t                                              21

<210> SEQ ID NO 61
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 61
```

```
acctcctgtc ctccaacttg t                                              21

<210> SEQ ID NO 62
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 62
tggtacagca acaggaggga t                                              21

<210> SEQ ID NO 63
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 63
atccctcctg ttgctgtacc a                                              21

<210> SEQ ID NO 64
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 64
agaagaactc cctcgcctc                                                 19

<210> SEQ ID NO 65
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 65
gaggcgaggg agttcttct                                                 19

<210> SEQ ID NO 66
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 66
gaagaagaac tccctcgcct c                                              21

<210> SEQ ID NO 67
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 67
gaggcgaggg agttcttctt c                                              21

<210> SEQ ID NO 68
<211> LENGTH: 23
<212> TYPE: DNA
```

```
<213> ORGANISM: Unknown Organism
<220> FEATURE:
<223> OTHER INFORMATION: Description of Unknown Organism: shRNA sequence

<400> SEQUENCE: 68
tagaagaaga actccctcgc ctc                                              23

<210> SEQ ID NO 69
<211> LENGTH: 23
<212> TYPE: DNA
<213> ORGANISM: Unknown Organism
<220> FEATURE:
<223> OTHER INFORMATION: Description of Unknown Organism: shRNA sequence

<400> SEQUENCE: 69
gaggcgaggg agttcttctt cta                                              23

<210> SEQ ID NO 70
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 70
cctagaagaa gaactccctc gcctc                                            25

<210> SEQ ID NO 71
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 71
gaggcgaggg agttcttctt ctagg                                            25

<210> SEQ ID NO 72
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 72
cctaggagaa ggactccctt gcctc                                            25

<210> SEQ ID NO 73
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 73
gaggcgaggg agttcttctt ctagg                                            25

<210> SEQ ID NO 74
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 74
cctagaagaa gaactccctc gcctc                                            25
```

<210> SEQ ID NO 75
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 75
gaggcgaggg agttcttctt ctagg                                              25

<210> SEQ ID NO 76
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 76
cctaggagaa ggactccctt gcctc                                              25

<210> SEQ ID NO 77
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 77
gaggcaaggg agtccttctc ctagg                                              25

<210> SEQ ID NO 78
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 78
cctaggagaa ggactccctt gcctc                                              25

<210> SEQ ID NO 79
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 79
gaggcgaggg agttcttctt ctagg                                              25

<210> SEQ ID NO 80
<211> LENGTH: 25
<212> TYPE: DNA
<213> ORGANISM: Unknown Organism
<220> FEATURE:
<223> OTHER INFORMATION: Description of Unknown Organism: shRNA sequence

<400> SEQUENCE: 80
cctagaagaa gaactccctc gcctc                                              25

<210> SEQ ID NO 81
<211> LENGTH: 25
<212> TYPE: DNA
<213> ORGANISM: Unknown Organism
<220> FEATURE:

```
<223> OTHER INFORMATION: Description of Unknown Organism: shRNA sequence

<400> SEQUENCE: 81
gaggcaaggg agtccttctc ctagg                                              25

<210> SEQ ID NO 82
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 82
cctagaagaa gaactccct                                                     19

<210> SEQ ID NO 83
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 83
agggagttct tcttctagg                                                     19

<210> SEQ ID NO 84
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 84
gaagaagaac tccctcgcc                                                     19

<210> SEQ ID NO 85
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 85
ggcgagggag ttcttcttc                                                     19

<210> SEQ ID NO 86
<211> LENGTH: 20
<212> TYPE: DNA
<213> ORGANISM: Unknown Organism
<220> FEATURE:
<223> OTHER INFORMATION: Description of Unknown Organism: shRNA sequence

<400> SEQUENCE: 86
gcgaaaggcc ttgtggtact                                                    20

<210> SEQ ID NO 87
<211> LENGTH: 20
<212> TYPE: DNA
<213> ORGANISM: Unknown Organism
<220> FEATURE:
<223> OTHER INFORMATION: Description of Unknown Organism: shRNA sequence

<400> SEQUENCE: 87
agtaccacaa ggcctttcgc                                                    20
```

```
<210> SEQ ID NO 88
<211> LENGTH: 21
<212> TYPE: DNA
<213> ORGANISM: Unknown Organism
<220> FEATURE:
<223> OTHER INFORMATION: Description of Unknown Organism: shRNA sequence

<400> SEQUENCE: 88
gtgcacggtc tacgagacct c                                              21

<210> SEQ ID NO 89
<211> LENGTH: 20
<212> TYPE: DNA
<213> ORGANISM: Unknown Organism
<220> FEATURE:
<223> OTHER INFORMATION: Description of Unknown Organism: shRNA sequence

<400> SEQUENCE: 89
gaggtctcgt agaccgtgca                                                20

<210> SEQ ID NO 90
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 90
attggagtga gtttaagct                                                 19

<210> SEQ ID NO 91
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 91
agcttaaact cactccaat                                                 19

<210> SEQ ID NO 92
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 92
ggtatgagct gatcaagta                                                 19

<210> SEQ ID NO 93
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 93
tacttgatca gctcatacc                                                 19

<210> SEQ ID NO 94
<211> LENGTH: 19
<212> TYPE: DNA
<213> ORGANISM: Unknown Organism
<220> FEATURE:
<223> OTHER INFORMATION: Description of Unknown Organism: shRNA sequence
```

```
<400> SEQUENCE: 94
ggcgacatct acttcaaca                                                19

<210> SEQ ID NO 95
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 95
tgttgaagta gatgtcgcc                                                19

<210> SEQ ID NO 96
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 96
gtggaaatct cctgccata                                                19

<210> SEQ ID NO 97
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 97
tatggcagga gatttccac                                                19

<210> SEQ ID NO 98
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 98
gttctctgcc tcccgattc                                                19

<210> SEQ ID NO 99
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 99
gaatcgggag gcagagaac                                                19

<210> SEQ ID NO 100
<211> LENGTH: 19
<212> TYPE: DNA
<213> ORGANISM: Unknown Organism
<220> FEATURE:
<223> OTHER INFORMATION: Description of Unknown Organism: shRNA sequence

<400> SEQUENCE: 100
gatcgaatgt gtacttcga                                                19

<210> SEQ ID NO 101
<211> LENGTH: 19
```

```
<212> TYPE: DNA
<213> ORGANISM: Unknown Organism
<220> FEATURE:
<223> OTHER INFORMATION: Description of Unknown Organism: shRNA sequence

<400> SEQUENCE: 101
tcgaagtaca cattcgatc                                                      19
```